United States Patent
Praly et al.

(10) Patent No.: US 9,199,931 B2
(45) Date of Patent: Dec. 1, 2015

(54) PYRROLIDINE DERIVATIVES

(71) Applicants: UNIVERSITE CLAUDE BERNARD LYON I, Villeurbanne Cedex (FR); INSTITUT NATIONAL DES SCIENCES APPLIQUEES DE LYON, Villeurbanne Cedex (FR); CENTRE NATIONAL DE LA RECHERCHE SCIENTIFIQUE, Paris Cedex (FR); CPE LYON FCR, Villeurbanne (FR)

(72) Inventors: Jean-Pierre Praly, Vourles (FR); Kaiss Aouadi, Le Kef (TN); Samy Cecioni, Oullins (FR); Luc Denoroy, Villeurbanne (FR); Sandrine Parrot, Villeurbanne (FR)

(73) Assignees: UNIVERSITE CLAUDE BERNARD LYON I, Villeurbanne; INSTITUT NATIONAL DES SCIENCES APPLIQUEES DE LYON, Villeurbanne; CENTRE NATIONAL DE LA RECHERCHE SCIENTIFIQUE, Paris (FR); CPE LYON FCR, Villeurbanne (FR)

( * ) Notice: Subject to any disclaimer, the term of this patent is extended or adjusted under 35 U.S.C. 154(b) by 0 days.

(21) Appl. No.: 14/412,050

(22) PCT Filed: Jun. 28, 2013

(86) PCT No.: PCT/FR2013/051524
§ 371 (c)(1),
(2) Date: Dec. 30, 2014

(87) PCT Pub. No.: WO2014/006307
PCT Pub. Date: Jan. 9, 2014

(65) Prior Publication Data
US 2015/0175537 A1    Jun. 25, 2015

(30) Foreign Application Priority Data
Jul. 2, 2012    (FR) .................................... 12 56322

(51) Int. Cl.
C07D 207/12    (2006.01)

(52) U.S. Cl.
CPC .................................... *C07D 207/12* (2013.01)

(58) Field of Classification Search
CPC ...................................................... C07D 207/12
See application file for complete search history.

(56) References Cited

U.S. PATENT DOCUMENTS

| 5,888,996 A | 3/1999 | Farb |
| 2004/0259917 A1 | 12/2004 | Cosford et al. |
| 2009/0023935 A1* | 1/2009 | Gotoh et al. .................. 548/536 |

OTHER PUBLICATIONS

International Search Report dated Sep. 17, 2013, corresponding to International Patent Application PCT/FR2013/051524.

* cited by examiner

*Primary Examiner* — Robert Havlin
(74) *Attorney, Agent, or Firm* — Ladas & Parry LLP

(57) ABSTRACT

The present invention relates to novel pyrrolidine derivatives of formula (I):

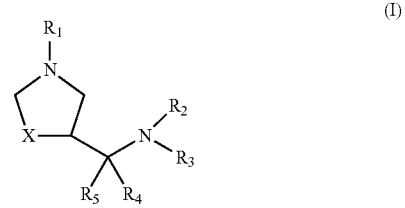

(I)

wherein $R_1$, $R_2$, $R_3$, $R_4$, $R_5$ and X are as defined in claim 1, optionally in a zwitterionic form, in the form of a pure optical isomer, or in the form of a mixture of optical isomers in any proportions, or in a form enriched with an optical isomer, as well as their pharmaceutically acceptable salts, solvates or hydrates, and pharmaceutical compositions containing such compounds. These compounds are notably useful for treating, in particular in human beings, epilepsy, ischemia, neurodegenerative diseases such as Parkinson's disease or Huntington's chorea, multiple sclerosis, Devic's disease, Alzheimer's disease, psychiatric diseases such as schizophrenia, depression, addiction, allodynia and hyperalgia.

12 Claims, 5 Drawing Sheets

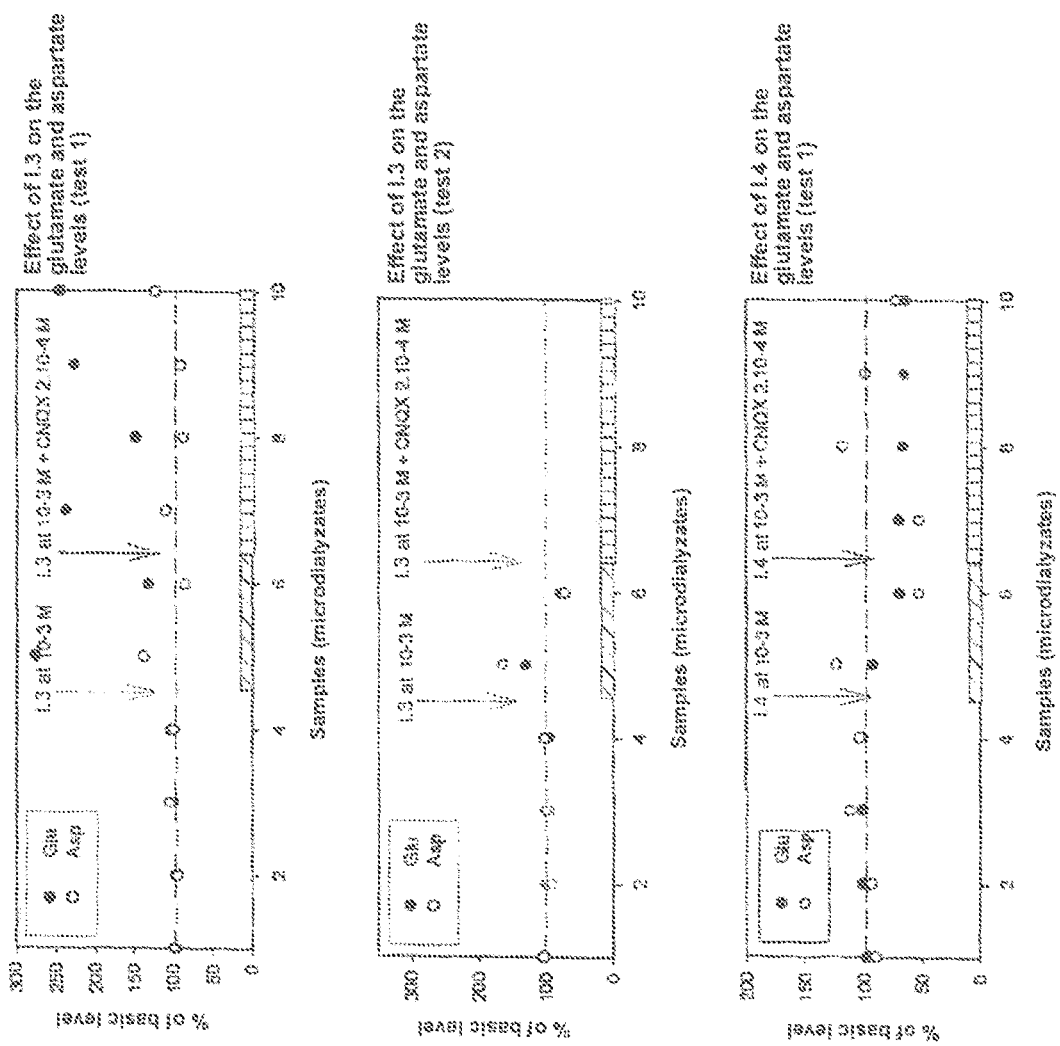

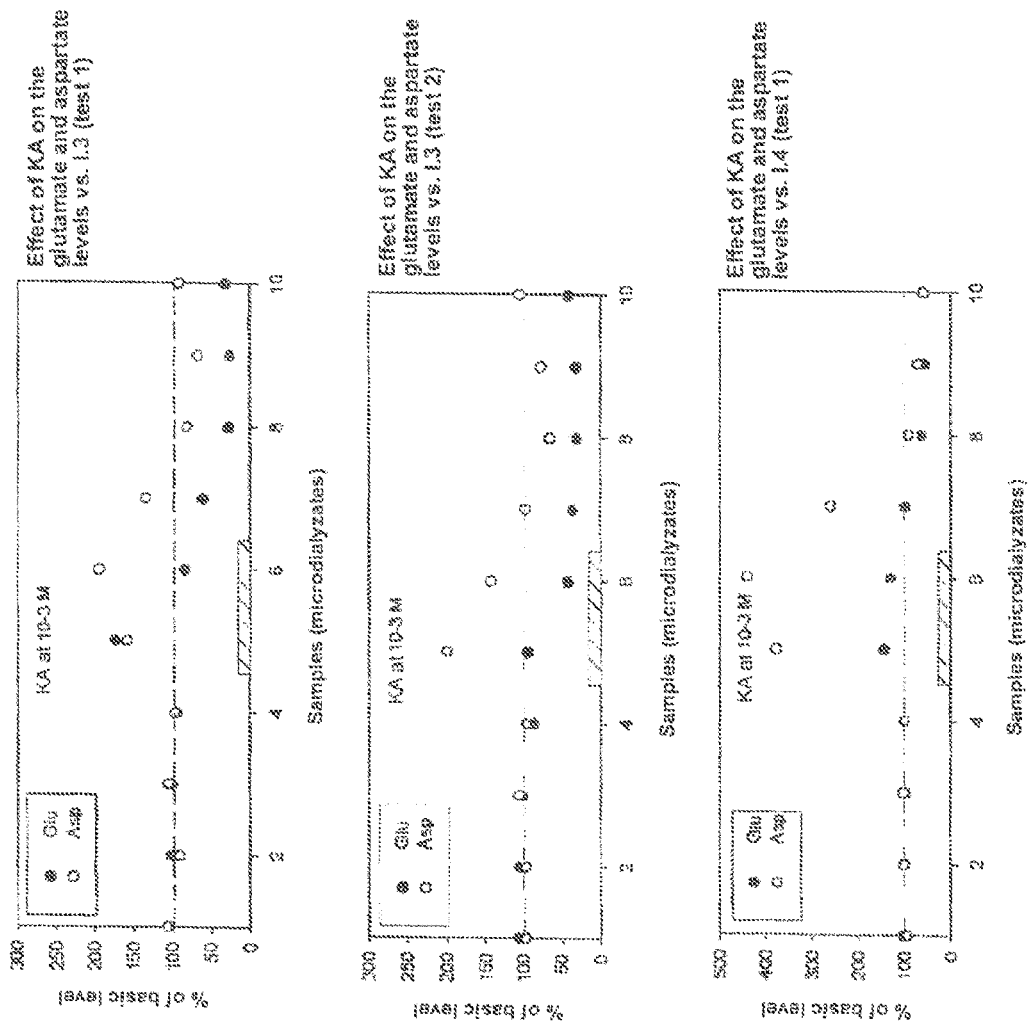

PYRROLIDINE DERIVATIVES

This application is a 371 of PCT/FR2013/051524, filed on Jun. 28, 2013, which claims priority to French Application No. 1256322, filed Jul. 2, 2012.

The present invention relates to the technical field for treating diseases of the central nervous system. More specifically, the object of the invention is novel pyrrolidine derivatives, pharmaceutical compositions containing such compounds, and such compounds, as a drug, and notably for their use in treating, in particular in humans, epilepsy, ischemia, a neurodegenerative disease such as Parkinson's disease or Huntington's chorea, multiple sclerosis, Devic's disease (NMO), Alzheimer's disease, a psychiatric disease such as schizophrenia, depression, addiction, allodynia, hyperalgia, pain (analgesia), cancer of an organ or of a peripheral tissue, obesity, musculoskeletal disorder, cardio-vascular disease or a disease of the digestive tracts or for controlling food intake.

Glutamic acid (Glu) and to a lesser extent, aspartic acid (Asp) are the major neurotransmitters of the central nervous system [1-2]. Both of these neurotransmitter amino adds are present in all the neuronal networks and have a ubiquitous anatomic distribution in the brain. They play a role in neurophysiologic processes such as like autonomic system control, motor functions, pain control, cognitive tasks, learning and memory, . . . . Experiments conducted on animal models of human diseases and data obtained in humans have revealed alterations of this type of neurotransmission in pathologies such as epilepsy, ischemia, neurodegenerative diseases (Parkinson, Huntington) or psychiatric diseases like schizophrenia [2-6]. These four main research themes are conventionally the subject of studies of the control of acido-aminergic neurones. Other pathologies are also known, as involving glutamate: mention may notably be made of multiple sclerosis, Devic's disease, Alzheimer's disease, depression, but also addiction, allodynia and hyperalgia [7].

There exist two large families of receptors (ionotropic and metabotropic) of glutamic acid and of aspartic acid. These receptors have been classified into 5 types (kainate and NMDA for ionotropic ones, group I, group II and groups III for metabotropic receptors) and their respective sub-types have been determined according to their affinities, intracellular couplings and/or anatomic localization (glutamate acts on all the sub-types, while aspartate only acts on NMDA receptors). Excitatory amino adds remain a primordial challenge in the search for pharmacologic targets selectively aiming at one, or sub-types of their receivers. For example, pharmacologic agents targeting the excitatory transmission of the amino adds were developed for treating epilepsies or for preventing toxicity induced by ischemia. Many commercial anti-epileptic substances have an amino-acid structure. As an example, mention may be made of Phenobarbital, Primidone, Phenyloin, among the older ones, and Acetazolamide, Zonisamide and Rufinamide from among the most recent ones. Antiepileptics similar to Gaba and derivatives of pyrrolidin-2-one are also active ingredients of commercial drugs for treating epilepsy. Mention may be made of Ethosuximide, Piracetam, Oxiracetam, Levetiracetam, Pramiracetam, Aniracetam and Nefiracetam.

Other derivatives of pyrrolidin-2-one are also known for other activities. Penmacric add from seeds of *Pentachlethra macrophylla* is described for its food and medicinal use [8], Alahopsin is an antibiotic used against diverse Gram positive and negative bacteria and also an inhibitor of propyl collagen hydroxylase [9], just like dealanylalahopsin [9, 10].

Nevertheless, there always exists a need for novel compounds having a benefit for treating diseases of the central nervous system, and in particular for novel compounds which have a modulating activity on the rates of extracellular glutamate and aspartate.

The inventors of the present patent application were interested in other derivatives of pyrrolidine, other than derivatives of pyrrolidin-2-one.

In this context, the present invention relates to derivatives of pyrrolidine of formula (I):

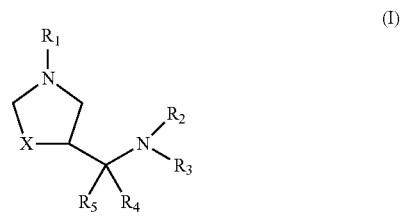

wherein:
$R_1$ represents a hydrogen atom, a $(C_1\text{-}C_6)$alkyl or $C(O)(C_1\text{-}C_6)$alkyl group,
$R_2$ and $R_3$, either identical or different, represent, in each independently of each other, a hydrogen atom or a $(C_1\text{-}C_6)$alkyl group; or else $R_2$=H and $R_3$=$C(O)(C_1\text{-}C_6)$alkyl,
$R_4$ represents —COOH, —CN, —COM, —C(=NOH)NH$_2$, —CH$_2$NH$_2$, —CH$_2$OH, —C(O)NH$_2$, —C(O)NHR$_a$, —COSR$_a$, with $R_a$ which represents a $(C_1\text{-}C_6)$ alkyl group, or else $R_1$ represents a tetrazole or 1,2,4-oxadiazole group,
$R_5$ represents a hydrogen atom or a $(C_1\text{-}C_6)$alkyl group,
X represents C(O)— or CHR$_b$—, with R$_b$ which represents —OR$_c$ or —OC(O)R$_c$,
R$_c$ representing a hydrogen atom or a $(C_1\text{-}C_6)$alkyl group, optionally in a zwitterionic form,
in the form of a pure optical isomer or in the form of a mixture of optical isomers in any proportions, or in a form enriched with an optical isomer, as well as their pharmaceutically acceptable salts, solvates or hydrates.

In the definition of the compounds according to the invention, by alkyl group, is meant a linear or branched saturated hydrocarbon chain. As an example of an alkyl group comprising from 1 to 6 carbon atoms, designated as $(C_1\text{-}C_6)$alkyl, mention may notably be made of the methyl, ethyl, n-propyl, isopropyl, n-butyl, tert-butyl, sec-butyl, n-pentyl, n-hexyl groups.

BRIEF DESCRIPTION OF THE DRAWINGS

FIG. 2A shows a comparison of the effects of I.3 and I.4 with kainate (KA), tested in vivo on the brain (brain structure: striatum) of anesthetized entire animals. The results are expressed in a percentage of the average of four values preceding administration of the KA.

FIG. 2B shows a comparison of the effects of I.3 and I.4 without kainate (KA), tested in vivo on the brain (brain structure: striatum) of anesthetized entire animals. The results are expressed in a percentage of the average of four values preceding administration of the KA.

Figure 1A:
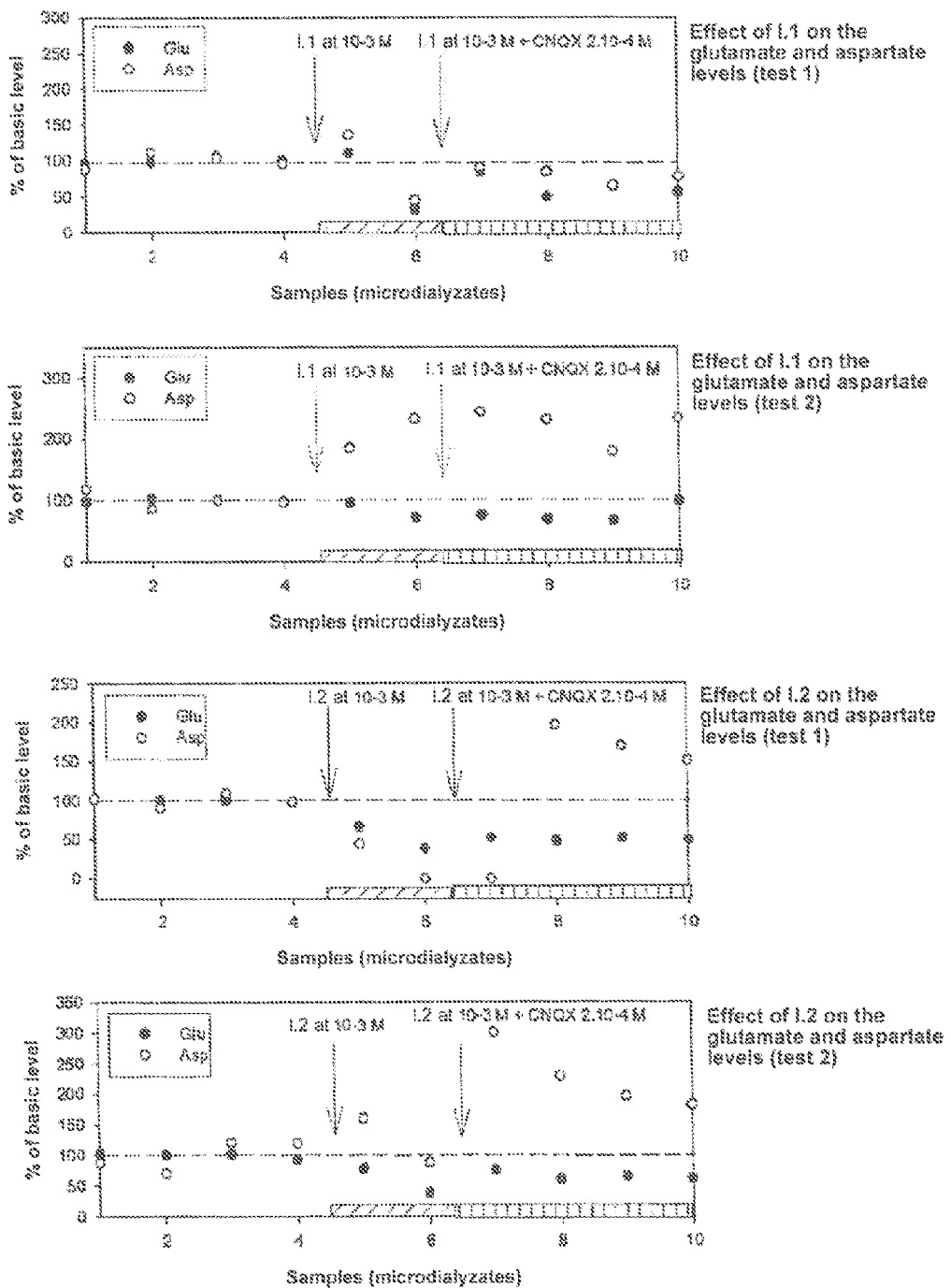
FIG. 1A shows a comparison of the effects of the molecules I.1 and I.2 with kainate (KA), tested in vivo on the brain (brain structure: striatum) of anesthetized entire animals. The results are expressed in a percentage of the average of four values preceding administration of the KA.
Figure 1B:
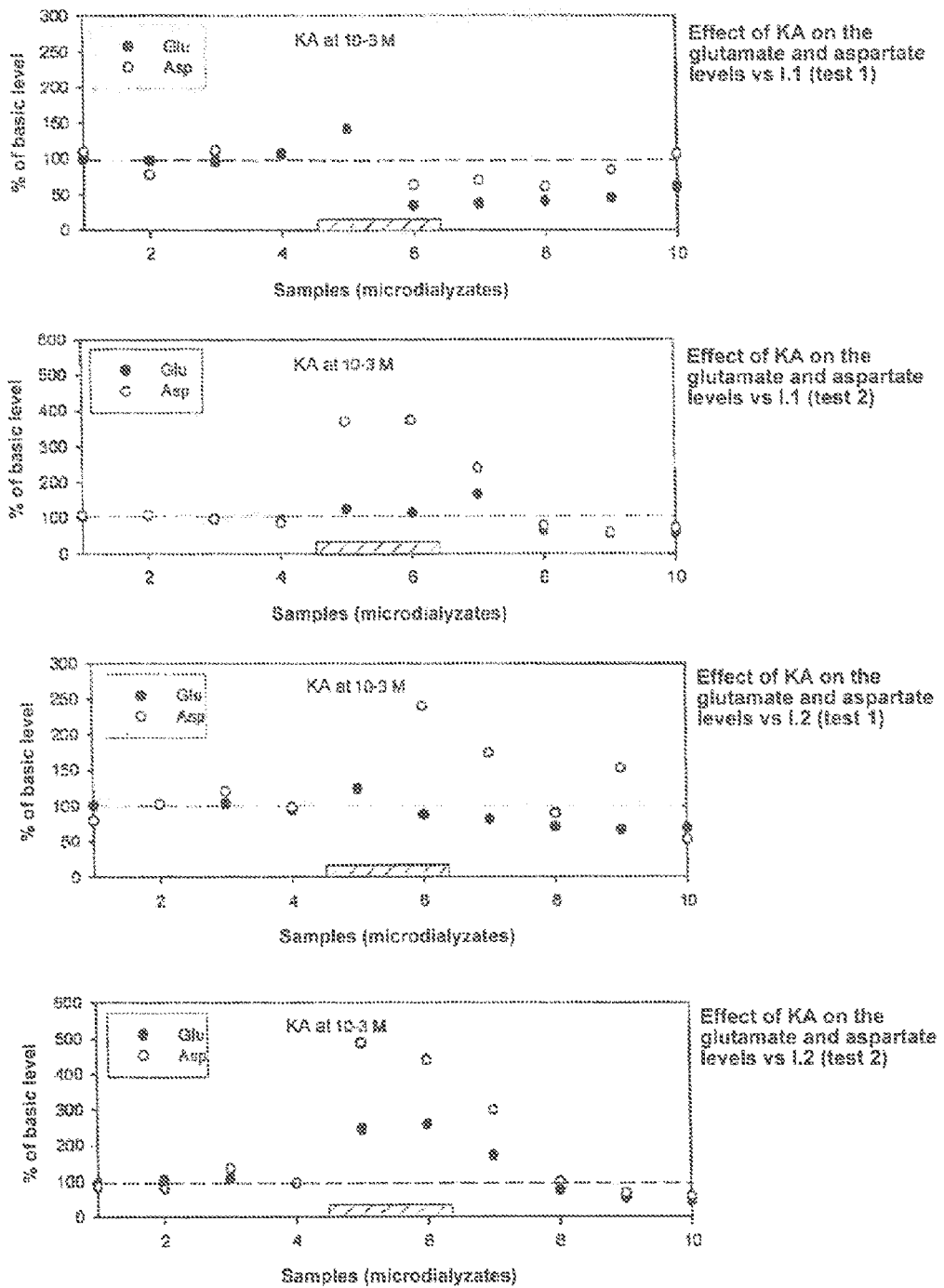
FIG. 1B shows a comparison of the effects of the molecules I.1 and I.2 without kainate (KA), tested in vivo on the brain (brain structure: striatum) of anesthetized entire animals. The results are expressed in a percentage of the average of four values preceding administration of the KA.

According to preferred embodiments, X represents —CHR$_b$, with notably R$_b$=OH. In this case, the derivatives of pyrrolidine according to the invention may notably fit the formula (Ia):

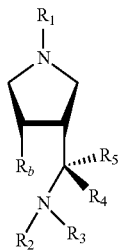
(Ia)

wherein R$_1$, R$_2$, R$_3$, R$_4$, R$_5$ and R$_b$ are as defined for the compounds of formula (I), optionally as a pharmaceutically acceptable salt, solvate or hydrate, or formula (Ib):

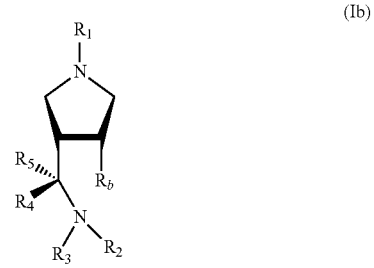
(Ib)

wherein R$_1$, R$_2$, R$_3$, R$_4$, R$_5$ and R$_b$ are as defined for the compounds of formula (I), optionally as a pharmaceutically acceptable salt, solvate or hydrate.

According to particular embodiments, the compounds of formulae (I), (Ia) or (Ib), have a feature below or a combination of the features below, or even all the features below:
- R$_1$ is a hydrogen atom;
- R$_2$=H and R$_3$ represents a hydrogen atom or a methyl or —C(O)CH$_3$ group;
- R$_4$ represents —COOH, —C(O)NHCH$_3$ or —CH$_2$NH$_2$;
- R$_5$ is a hydrogen atom,
- it appears in a salified or zwitterionic form including a quaternary ammonium.

The compounds used within the scope of the invention are prepared according to conventional techniques. They may notably be obtained according to methods similar to those used in the examples.

It is possible to use either a so-called chiral approach, or a so-called achiral synthesis, as explained below.

SCHEME 1 below, in which R'$_1$ represents R$_1$ as defined for (I), or a protective group of the benzyl type, illustrates the chiral approach.

SCHEME 1

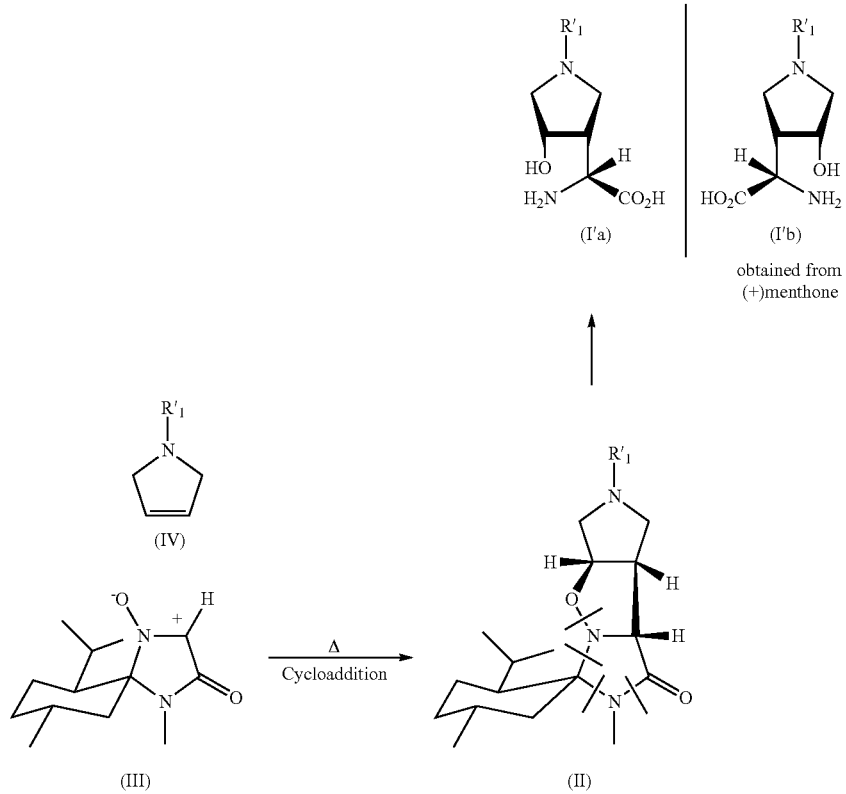

In a first step, a cycloaddition is achieved, notably at a temperature close to 110° C., optionally under activation from microwaves, of the nitrone (III) and of an alkene (IV) for leading to a cycloadduct (II) which, after a hydrogenolysis step under the action of hydrogen in the presence of a catalyst (for example palladium on coal) causing cleavage of the N—O bond, and an add hydrolysis (preferably with a mixture of acetic anhydride antacid acidified with $H_2SO_4$) and then basic hydrolysis, causing the cleavage of the three bonds at the nitrone as illustrated in the SCHEME 1 above, gives compounds (I'a) or (I'b). The compounds (I'a) and (I'b) correspond directly to compounds formula (Ia) or (Ib) or may be functionalized at the amino group or at the carboxylic acid group according to techniques well known to one skilled in the art. The function $NR'_1$ may also itself be deprotected or alkylated, in order to lead to the desired compounds according to conventional methods and the OH function may be alkylated in order to lead to a —$O(C_1-C_6)$alkyl group.

Another strategy may be adaptation, as in the examples, of the cleavage conditions in order to directly end up with the desired group(s) —$NR_2R_3$ and/or $R_4$.

The nitrones (III) may be obtained from chiral menthones (IV) according to SCHEME 2 below.

or as an aqueous solution), or of its commercial esters (ethyl esters) or easy to prepare (isopropyl esters) [12, 13, 14, 15, 16, 17, 18, 19, 20, 21, 22]. It is also possible, in the achiral approach, to achieve cycloaddition, not with a nitrone but with a nitrile oxide. Such nitrile oxides may be obtained from the corresponding aldehydes and may then be used in dipolar cycloadditions which, on alkenes give isoxazolines. By reduction, a cut of the N—O bond is obtained and simultaneously a reduction of the double bond [23] according to SCHEME 3 below wherein $R'_1$ represents $R_1$ as defined for (I), or a protective group of the benzyl type or of the tert-butoxycarbonyl (boc) type.

SCHEME 3

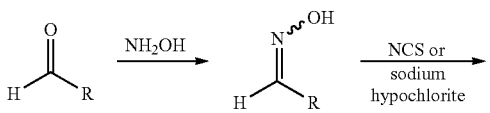

SCHEME 2

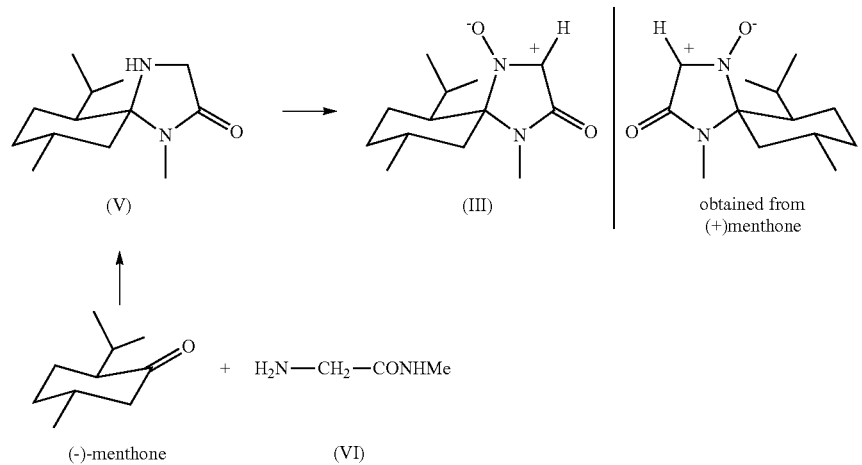

The introduction of the group $R_5$ different from hydrogen may be accomplished later on.

The nitrones (III) may be obtained from compounds (V) in the presence of meta-chloro-perbenzoic acid m-CPBA (preferably 2 equivalents) and of 3-chlorobenzoic add (which is a by-product of the oxidation reaction). The initial reagents are available commercially (notably 3-pyrroline and N-benzyl-3-pyrroline are commercial products) or easily accessible. The compounds (VI) may notably be obtained from the corresponding ester by reaction with methylamine on the glycine methyl ester hydrochloride, at a temperature of the order of 0 to 78° C., and notably at room temperature.

In the achiral approach, it is possible to either use nitrones, or nitrile oxides without any chirality. Many achiral equivalent glycine nitrones are available in the literature. Their synthesis is notably based on the formation of substituted cyanomethylamines, from halogenoacetonitrile and substituted amines, followed by oxidation into nitrones [11].

Another route for accessing suitable nitrones resorts to hydroxylamines reacting on the carbonyl function of glyoxylic acid (commercial glyoxylic add, either pure monohydrate, -continued

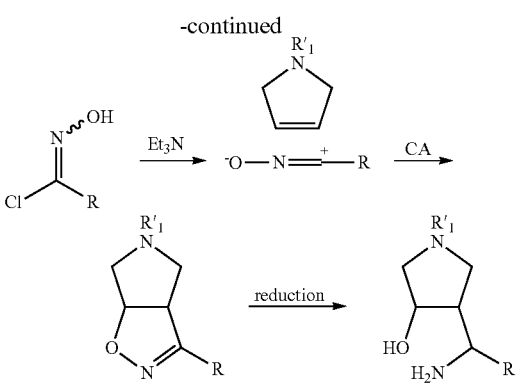

The compounds according to the invention may notably have two or three asymmetrical carbon atoms. Their different optical isomers are an integral part of the invention. The various compounds according to the invention may therefore be found in all the possible isomeric forms, notably as a mixture in all proportions, unless specified otherwise. According to a particular embodiment, the compounds according to the invention are found in a racemic form, both enantiomers being found in substantially equal proportions. According to another embodiment, the compounds of formula (I) of the invention may be found in a form enriched with a diastereoisomer or enantiomer, with a diastereoisomer or enantiomer excess of more than 80%, or even more than 95%, or even in a pure isomeric form i.e., with a diastereoisomer or enantiomer excess of more than 99%, or even more equal to 100%.

The compounds (I) may be isolated as isomers or in a form enriched with a diastereoisomer or enantiomer by conventional separation techniques: for example it is possible to use fractionated recrystallizations of a salt of the racemic with an optically active acid or base, the principle of which is well known or, most often, conventional chromatography techniques on a chiral or non-chiral phase. It is also possible as explained above to directly use a so-called chiral synthesis leading to the desired optical isomer.

The compounds of formula (I) above also comprise those in which one or several hydrogen, carbon or nitrogen atoms have been replaced with halogens, notably chlorine or fluorine including with their radioactive isotope for example tritium, carbon-14, or fluorine-18. Such marked compounds are useful in research, metabolism or pharmacokinetics studies, in biochemical tests.

The functional groups optionally present in the molecule of the compounds of formula (I) and in the reaction intermediates may be protected during synthesis, either permanently or temporarily, with protective groups which ensure an unequivocal synthesis of the expected compounds. The protection and deprotection reactions are carried out according to techniques well known to one skilled in the art. By temporary protective group of amines, alcohols or carboxylic adds, are meant protective groups such as those described in Protective Groups in Organic Synthesis, Greene T W and Wuts P. G. M., ed. John Wiley and Sons, 2006 and in Protecting Groups, Kocienski P J, 1994, Georg Thieve Verlag.

The salts of the compounds according to the invention are prepared according to techniques well known to one skilled in the art. The salts of the compounds of formula (I) according to present invention comprise those with acids or bases, depending on the substituents which are present. These acids or bases may be selected from mineral and organic acids and bases which allow separation or suitable crystallization of the compounds of formula (I), as well as pharmaceutically acceptable salts. As a suitable acid, mention may be made of oxalic acid or an optically active acid, for example tartaric acid, dibenzoyltartaric acid, mandelic acid or camphorsulfonic acid, and those which form physiologically acceptable salts, such as hydrochloride, hydrobromide, sulfate, hydrogensulfate, dihydrogenphosphate, maleate, fumarate, 2-naphthalenesulfonate, para-toluenesulfonate, mesylate, besylate, isothionate. As a suitable base, mention may be made of: lysine, arginine, meglumine, benethamine, benzathine and those which form physiologically acceptable salts, such as sodium, potassium, calcium salts.

As compounds in a hydrate form, mention may be made as an example of semi-hydrates, monohydrates and polyhydrates.

By solvate, is meant a form of the compound associated with one or several solvent molecules, notably used during its synthesis or during its purification, without however being in solution in the latter.

Within the scope of the invention, it was shown that the compounds of formula (I) in the form of a mixture of optical isomers in any proportions, or in a form enriched with an optical isomer, as well as their pharmaceutically acceptable salts, solvates or hydrates have immediate and significant effects on the extracellular glutamate and aspartate levels. The activity of the compound according to the invention corresponds to an increase or to a reduction in the glutamate and aspartate levels depending on the compounds. These effects are moreover highly dependent on the endogenous glutamate levels, as this was shown for the kainate, for example. In particular, most of the compounds according to the invention, and the compounds of formula (I.1) to (I.4) explicitly given in the examples, cause a reduction in the extracellular glutamate levels in rat brains, when the initial glutamate level is high, notably greater than 10 µmol/L. They may therefore be useful for treating pathologies corresponding to glutamatergic hyperactivity. By extrapolation from the concentrations used during the introduction of the compounds (I.1) to (I.4) by reverse dialysis, the activity range after peripheral administration is estimated as being between 5 and 100 mg/kg in animals.

The object of the present invention is also the compounds as defined earlier, for their use as a drug, and in particular for their use as a drug for treating epilepsy, ischemia, a neurodegenerative disease such as Parkinson's disease or Huntington's chorea, Alzheimer's disease, multiple sclerosis, Devic's disease, psychiatric disease such as schizophrenia, depression, addiction, allodynia, hyperalgia, pain (analgesia), cancer of an organ or of a peripheral tissue, obesity, a musculoskeletal disorder, a cardiovascular disease or a disease of the digestive tracts or for controlling food intake.

Within the scope of the invention, the use of the compounds according to the invention, in the treatment of human beings is particularly a target.

The pharmaceutical compositions comprising a compound as defined earlier, in association with at least one pharmaceutically acceptable excipient, are also an integral part of the invention.

The term of <<treatment>> refers to any prophylactic or suppressive therapeutic measure against a disease or disorder leading to a desirable clinical effect or to any beneficial effect, notably including the suppression or reduction of one or several symptoms, regression, slowing down or stopping the progression of the disease or of the disorder which is associated therewith.

By <<therapeutically effective amount>>, is meant any amount of a composition which improves one or several of the characteristic parameters of the treated disease.

Because of their activity, the compounds according to the invention, regardless of their isomeric form, may be used for making a drug intended for treating epilepsy, ischemia, a neurodegenerative disease such as Parkinson's disease or Huntington's chorea, Alzheimer's disease, multiple sclerosis, Devic's disease, a psychiatric disease such as schizophrenia, depression, addiction, allodynia, hyperalgia, pain (analgesia), cancer of an organ or of a peripheral tissue, obesity, a musculoskeletal disorder, a cardiovascular disease or a disease of the digestive tracts or for controlling food intake.

In particular, the compounds according to the invention will find a particular benefit for their use in the treatment of Parkinson's disease, epilepsy, addictive disorders or ischemia.

The object of the present invention is also pharmaceutical compositions which may be administered to animals, and in particular to humans, containing an effective dose of a compound according to the invention, and suitable excipient(s) notably according to European Pharmacopoeia 7$^{th}$ edition. The invention therefore relates to pharmaceutical compositions comprising a compound according to the invention, with at least one pharmaceutically acceptable excipient.

The excipients present in the pharmaceutical compositions according to the invention are selected according to the pharmaceutical form and to the desired administration method. In the pharmaceutical compositions of the present invention for oral, sublingual, subcutaneous, intramuscular, intravenous, intracartilage, topical, intratracheal, intranasal, transdermal, rectal or intraocular administration, the compounds according to the invention may be administered in the form of administration dosage unit forms, as a mixture with conventional pharmaceutical carriers, to animals and/or human beings for prophylaxial treatment of the diseases above. The suitable administration unit dosage forms comprise oral forms, such as tablets, gelatin capsules, powders, granules and oral solutions or suspensions, sublingual, buccal, intratracheal, intranasal administration forms, subcutaneous, intramuscular, intracartilage or intravenous administration forms and rectal administration forms. For topical application, the compounds according to the invention may be used in creams, ointments, patches or lotions.

In order to obtain the desired effect, the compound according to the invention will be present in the composition at a therapeutically effective dose, in particular for treating human beings. The active ingredient dose for example varies between 1 and 50 mg per kg of body weight of the treated patient and per day.

When a solid composition is prepared as tablets, the main active ingredient is mixed with a pharmaceutical carrier, such as gelatine, starch, lactose, magnesium stearate, talcum, gum arabic or the like. The tablets may be coated with saccharose, a cellulose derivative, or other suitable materials or further they may be treated so that they have prolonged or delayed activity and that they continuously release a predetermined amount of active ingredient.

A preparation in gelatin capsules is obtained by mixing the active ingredients with a diluent and by pouring the obtained mixture into soft or hard gelatin capsules.

Pharmaceutical compositions containing a compound according to the invention, may also appear as a liquid, for example solutions, emulsions, suspensions or syrups. The suitable liquid supports may for example be water, organic solvents such as glycerol or glycols, as well as mixtures thereof in varied proportions, in water.

A preparation as a syrup or elixir or for administration as drops may contain the active ingredient together with an acaloric sweetener, an antiseptic, as well as an agent giving taste and a suitable coloring agent. The powders or granules dispersible in water may contain the active ingredient in a mixture with dispersion agents or wetting agents, or suspending agents, such as polyvinylpyrrolidone, as well as with sweeteners or taste correcting agents.

Generally, the same alternatives as those indicated earlier for the compounds (I) are applicable mutatis mutandis to the drugs, compositions and uses applying these compounds.

The examples hereafter give the possibility of illustrating the invention, but have no limiting nature.

I. Chemical Synthesis:

Attribution [58:18] of the NMR signals follows the numbering indicated hereafter for the molecules 3, 4, 8, and 11.

The preparation of the compounds (I.1) to (I.4) is shown in SCHEME 4 hereafter,

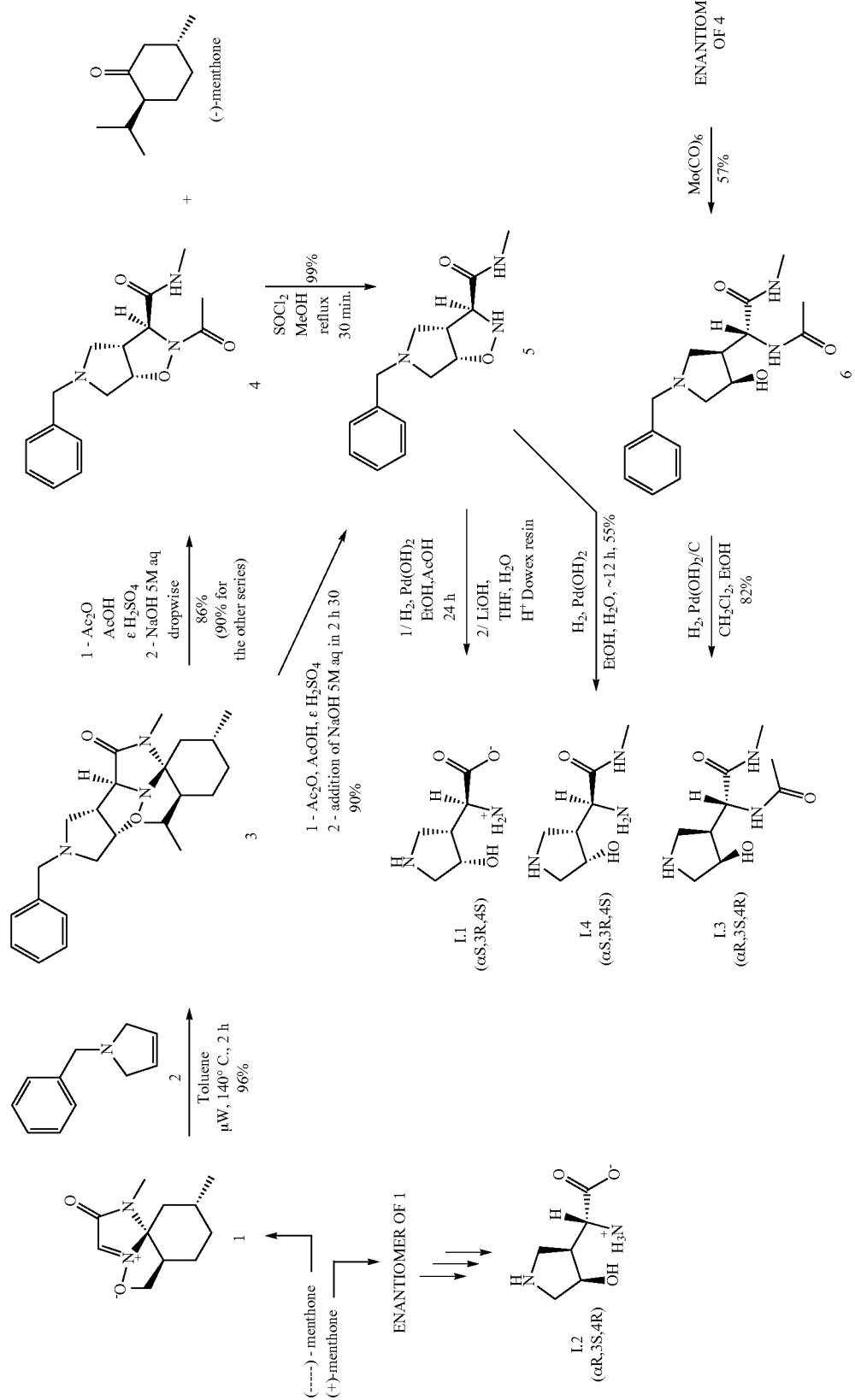
SCHEME 4

Preparation of the Compound I.1

(αS,3R,4S) 4-hydroxy α-amino acetic 3-pyrrolidine acid or (αS,3R,4S) α-amino-(4-hydroxy-pyrrolidin-3-yl)acetic acid

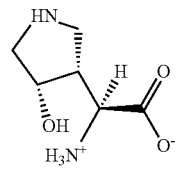

Cycloaddition of the nitrone 1 (corresponding to the compounds of formula (III)) on commercial N-Bn-3-pyrroline 2 (corresponding to the compounds of formula (IV)): synthesis of 3 (corresponding to the compounds of formula (II)):

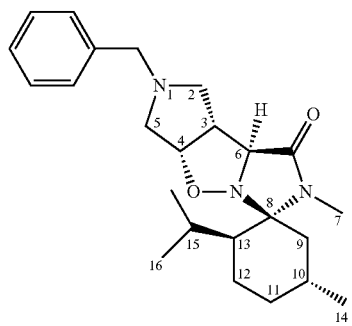 [SMILES: CC(C)[C@@H]1CC[C@@H](C)C[C@@]12N(C)C(=O)[C@@H]1[C@H]3CN(Cc4ccccc4)C[C@H]3ON12]

The nitrone 1 (392 mg, 1.64 mmol) [24, 25] and commercial N-Bn-3-pyrroline 2 in excess (314 mg, 1.97 mmol, 1.2 equiv.) are introduced into a flask adapted to a Biotage Initiator microwave reactor. After having filled the flask with argon, 2.5 ml of anhydrous toluene are poured therein. The flask, sealed with a septum and mounted in the microwave apparatus is irradiated with the instruction of maintaining a temperature of 140° C. for 2 h in order to totally convert the nitrone 1. Once the flask is cooled, the reaction crude product is concentrated and then purified by flash chromatography on a silica column (ethyl acetate) in order to lead to the cycloadduct 3 (625 mg, 1.57 mmol) with a yield of 96% and total stereoselectivity (the reaction was conducted on a scale of 5 grams with similar results).

Single crystals of the compound 3 were obtained from a diethyl ether solution saturated with 3, left in the cold (freezer).

$R_f$=0.48 (EtOAc). $[α]_D$=+40.4 (c 1.1, $CH_2Cl_2$). $^1H$ NMR (400 MHz, $CDCl_3$): δ 7.37-7.20 (m, 5H, CH-ar), 4.59 (td, J=7.0 Hz, J=3.0 Hz, 1H, H-4), 3.71-3.49 (m, 3H, $NCH_2Ph$, H-6), 3.42 (dd, J=10.3 Hz, J=6.6 Hz, 1H, H-3), 2.78 (dd, J=10.3 Hz, J=3.0 Hz, 1H, H-5), 2.75-2.69 (m, 4H, $NCH_3$, H-2), 2.65 (dd, J=9.4 Hz, J=3.7 Hz, 1H, H-2', 2.58 (dd, J=9.9 Hz, J=6.6 Hz, 1H, H-5'), 2.14-2.08 (m, 1H, H-9), 2.00 (dtt, J=12.9 Hz, J=6.5 Hz, J=3.3 Hz, 1H, H-10), 1.90-1.78 (m, 2H, H-11, H-12), 1.68-1.59 (m, 1H, H-12'), 1.48 (dt, J=13.5 Hz, J=6.7 Hz, 1H, H-15), 1.38 (dd, J=12.1 Hz, J=3.2 Hz, 1H, H-13), 1.18 (t, J=12.3 Hz, 1H, H-9'), 0.95-0.85 (m, 10H, H-11', H-14, H-16) ppm. $^{13}C$ NMR (100 MHz, $CDCl_3$): δ 172.8 (C=O), 138.9 ($C^{IV}$-ar), 128.6 (CH-ar), 128.3 (CH-ar), 127.1 (CH-ar), 88.0 (C-8), 79.6 (C-4), 71.9 (C-6), 59.6 ($NCH_2Ph$), 59.4 (C-5), 59.3 (C-2), 49.1 (C-3), 48.2 (C-13), 41.0 (C-9), 35.0 (C-11), 29.0 (C-10), 25.9 ($NCH_3$), 24.5 (C-15), 24.2 ($CH_3$), 22.6 (C-12), 22.4 ($CH_3$), 18.7 ($CH_3$) ppm. HR-ESI-QToF MS (positive method): m/z calcul. for $C_{24}H_{36}N_3O_2$ $[M+H]^+$ 398.2802. found 398.2806.

Acetolysis of compound 3 into a heterobicycle 4:

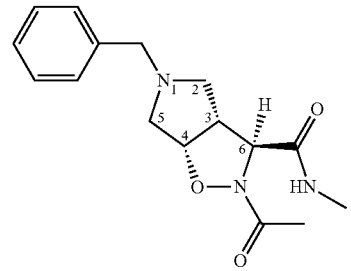 [SMILES: CNC(=O)[C@@H]1[C@H]2CN(Cc3ccccc3)C[C@H]2ON1C(C)=O]

Acetolysis of compound 3 takes place by adding a few drops (~6 drops) of concentrated sulfuric acid (95% $H_2SO_4$) to a reaction mixture containing 3 (226 mg, 0.57 mmol), acetic acid (3 ml) and acetic anhydride (3 ml), and then heating the medium to 60° C. for 6 h 30 min under argon. Once it has returned to room temperature, the medium is cooled in an ice bath at 0° C., and then the acid species are neutralized with a 5M soda solution (slow addition with control of the pH). When the pH is about 8, the medium is poured into a solution saturated with sodium bicarbonate $NaHCO_3$ (300 ml) and then a liquid-liquid extraction (dichloromethane, 5×50 ml) is carried out. After concentration and drying, the raw product is purified by flash chromatography on silica (ethyl acetate) in order to obtain the molecule 4 (148 mg, 0.49 mmol) with a yield of 86% (90% for the enantiomer ent-4). Among the fractions eluted at the head, the chiral auxiliary (−)-menthane 1 may be recovered and reused (recovery rate of 80% on the hydrolysis of 3 into 4 plus menthone).

$R_f$=0.28 (EtOAc). $[α]_D$=−14.2 (c 1, $CH_2Cl_2$). $^1H$ NMR (400 MHz, $CDCl_3$): δ 7.34-7.20 (m, 5H, CH-ar), 6.44 (bs, 1H, $NHCH_3$), 4.97 (bs 1H, H-6), 4.71 (dd, J=7.1 Hz, J=4.8 Hz, 1H, H-4), 3.62 (t, J=7.1 Hz, 1H, H-3), 3.57 (d, J=12.7 Hz, 1H, ½$NCH_2Ph$), 3.33 (d, J=12.7 Hz, 1H, ½$NCH_2Ph$), 3.10-2.99 (m, 2H, H-2, H-5), 2.79 (d, J=4.9 Hz, 3H, $NCH_3$), 2.34 (dd, J=10.0 Hz, J=7.1 Hz, 1H, H-2', 2.19 (dd, J=11.6 Hz, J=4.8 Hz, 1H, H-5'), 2.09 (s, 3H, $NC(O)CH_3$) ppm. $^{13}C$ NMR (100 MHz, $CDCl_3$): δ 175.7 (MeNC=O), 169.8 ($C(O)NHCH_3$), 138.1 ($C^{IV}$-ar), 128.9 (CH-ar), 128.5 (CH-ar), 127.5 (CH-ar), 85.0 (C-4), 66.2 (C-6), 60.7 (C-5), 60.4 (C-2), 59.9 ($NCH_2Ph$), 48.4 (C-3), 26.4 ($NCH_3$), 21.2 ($C(O)CH_3$) ppm. HR-ESI-QToF MS (positive method): m/z calcul. for $C_{16}H_{22}N_3O_3[M+H]^+$ 304.1656. found 304.1667.

N-Deacetylation from 4 into 5:

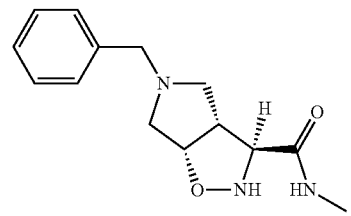 [SMILES: CNC(=O)[C@H]1NO[C@@H]2CN(Cc3ccccc3)C[C@H]12]

In order to facilitate cleavage of the N—O bond, it is preferable that the nitrogen atom be deacetylated. N-deacetylation is achieved by adding 4 (122 mg, 0.40 mmol) dissolved in 4 ml of dichloromethane to a solution of thionyl chloride $SOCl_2$ (151 µl, 5.2 equiv.) in freshly distilled methanol (3 ml), the solution having been stirred beforehand for 10 min at 0° C. (release of anhydrous hydrochloric acid). After 15 min at 0° C., the medium is left so as to return to room temperature, and then is refluxed by heating for 1 h. After cooling and adding a solution of sodium carbonate $Na_2CO_3$ at 5% (4 ml), the aqueous phase is extracted with ethyl acetate (2×30 ml). The organic phase is again washed with a 5% sodium carbonate solution (2×40 ml), with re-extraction of the aqueous phase with dichloromethane (2×20 ml). Evaporation of the solvents and freeze-drying give the compound 5 (104 mg, 0.4 mmol, 99%) i.e. quantitatively.

$R_f$=0.74 ($CH_2Cl_2$/IPA, 1/1). $[\alpha]_D$=+10.9 (c 1.3, $CH_2Cl_2$). $^1$H NMR (400 MHz, $CDCl_3$): δ 7.37-7.23 (m, 5H, CH-ar), 7.13 (bs, 1H, $NHCH_3$), 6.22 (d, J=3.9 Hz, 1H, ONHR), 4.62 (dd, J=6.6 Hz, J=4.8 Hz, 1H, H-4), 3.66 (bs 1H, H-6), 3.62 (t, J=6.7 Hz, 1H, H-3), 3.48 (d, J=6.1 Hz, 2H, $NCH_2Ph$), 3.07 (d, J=10.9 Hz, 1H, H-5), 3.00 (d, J=9.9 Hz, 1H, H-2), 2.79 (d, J=5.0 Hz, 3H, NC/6), 2.37 (dd, J=9.9 Hz, J=6.7 Hz, 1H, H-2', 2.21 (dd, J=10.9 Hz, J=4.9 Hz, 1H, H-5') ppm. $^{13}$C NMR (100 MHz, $CDCl_3$): δ 171.2 (C=O), 138.4 ($C^{IV}$-ar), 128.6 (CH-ar), 128.5 (CH-ar), 127.4 (CH-ar), 83.7 (C-4), 71.0 (C-6), 61.8 (C-5), 60.8 (C-2), 59.9 ($NCH_2Ph$), 50.2 (C-3), 26.0 ($NCH_3$) ppm. HR-ESI-QToF MS (positive method): m/z calcul. for $C_{14}H_{20}N_3O_2$ [M+H]$^+$ 262.1550. found 262.1553.

Direct acetolysis of compound 3 into the heterobicycle 5:

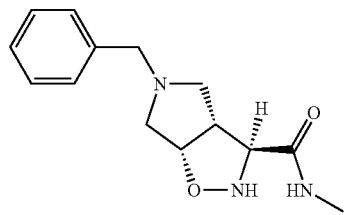 [SMILES: CNC(=O)[C@H]1NO[C@@H]2CN(Cc3ccccc3)C[C@H]12]

Acetolysis of compound 3 is achieved in a way close to the conversion of 3 into 4, by adding 0.8 ml of concentrated sulfuric acid (95% $H_2SO_4$) to a reaction mixture containing the compound 3 (542 mg, 1.36 mmol) acetic acid (7.2 ml) and acetic anhydride (7.2 ml), and then heating the medium to 46° C. for 6 h 30 min under argon. Once it has returned to room temperature, the reaction mixture is cooled in an ice bath at 0° C., and then the add species are neutralized with a 5M soda solution (drop wise addition over 2 h 30 min). When the pH is of about 8, the medium is poured into a solution saturated with sodium bicarbonate $NaHCO_3$ (700 ml) and then a liquid-liquid extraction (dichloromethane, 5×100 ml) is carried out. After concentration and drying, the crude product which contains trace amounts of the N-acetylated compound 4 is purified by flash chromatography on silica, in order to obtain 5 (320 mg, 90%).

Debenzylation and reducing opening of the N—O bond of 5 followed by basic hydrolysis: obtaining the compound I.1:

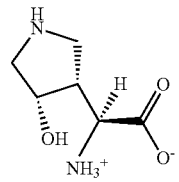

(αS,3R,4S) 4-hydroxy, α-amino, 3-pyrrolidine-acetic acid or (αS,3R,4S) α-amino-(4-hydroxy-pyrrolidin-3-yl)acetic acid A flask of 100 ml is used, which is filled with argon after having introduced therein the compound 5 (112 mg, 0.43 mmol). Ethanol (10 ml) and dichloromethane (6 ml) followed by 45 mg of palladium hydroxide hydrate $Pd(OH)_2$/C at 20% (45 mg) are added therein under argon. The flask is filled with hydrogen (1 atm) 5 vacuum and hydrogen admission cycles. After 3 h of stirring, it is seen (TLC) that the reaction is partial, A 100 µl of acetic acid AcOH circa 4 equiv. are added, and stirring is continued for a further 24 h under hydrogen. Catalyst is removed by filtration on Celite. After concentration of the reaction crude, the intermediate N-methylamide derivative is subject to basic hydrolysis in the presence of lithine (180 mg, 4.3 mmol, 10 equiv.) in a THF:$H_2O$ mixture (1/1, v/v, 8 ml) for 3 h. After evaporation, the crude lithium salt is subject to chromatography on a preconditioned C-18 silica column (adapted to automated equipment Combiflash), eluted with water, followed by passing over an ion exchange resin (Dowex 50W X8), the resin being, after deposition of the product, successively washed with water, and then with ammonia water (~10 ml at 2.5 and then 10 ml at 5%). The dry evaporation of the fractions containing the ammonium salt (TLC n-butanol/acetic acid/water, 3/1/1 with disclosure by dipping into a solution of ninhydrin in n-butanol, and then by heating) followed by passing over a C-18 column (ultrapure water) gives the possibility of obtaining the zwitterionic species I.1 with a yield of 57% over 2 steps (50% for the enantiomer) $R_f$=0.18 (n-BuOH/$H_2O$/AcOH, 3/1/1). $[\alpha]_D$=4.2 (c 0.5, DMSO/$H_2O$, 4/1), $^1$H NMR (400 MHz, $D_2O$): δ 4.58 (t, J=3.0 Hz, 1H, H-4), 3.54 (d 1H, J=9.5 Hz, H-6), 3.44 (dd, J=8.6 Hz, J=11.8 Hz, 1H, H-2), 3.39-3.36 (m, 2H, H-5, H-5), 3.29 (d, J=11.8 Hz, 1H, H-2'), 2.46 (ddd, J=3.8 Hz, J=9.1 Hz, J=12.4 Hz, 1H, H-3) ppm. $^{13}$C NMR (100 MHz, $D_2O$) δ 178.6 (C=O), 69.8 (C-4), 54.0 (C-6), 53.7 (C-5), 46.4 (C-3), 46.1 (C-2) ppm. HR-ESI-QToF MS (positive method): m/Z calcul. for $C_6H_{13}N_2O_3$ [M+H]$^+$ 161.0921. found 161.0924. The compound I.2 ((αR,3S,4R) 4-hydroxy, α-amino, 3-pyrrolidine-acetic acid or (αR,3S,4R) α-amino-(4-hydroxy-pyrrolidin-3-yl)acetic acid is prepared according to a route similar to the preceding one towards the enantiomer I.1.

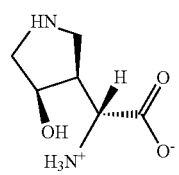

It is theoretically identical with the data for 1.1 except for the rotatory power [alpha] which is of an opposite sign $R_f$=0.18 (nBuOH/$H_2O$/AcOH, 3/1/1). $[\alpha]_D$=-4.1 (c 0.9, DMSO/$H_2O$, 4/1). $^1$H NMR (400 MHz, $D_2O$): δ 4.58 (t, J=2.9 Hz, 1H, H-4), 3.55 (d 1H, J=9.5 Hz, H-6), 3.45 (dd, J=8.7 Hz, J=11.8 Hz, 1H, H-2), 3.39-3.36 (m, 2H, H-5, H-5, 3.30 (d, J=11.8 Hz, 1H, H-2', 2.46 (ddd, J=3.8 Hz, J=9.0 Hz, J=12.2 Hz, 1H, H-3) ppm. $^{13}$C NMR (100 MHz, D$_2$O): δ 178.4 (C=O), 69.8 (C-4), 53.9 (C-6), 53.7 (C-5), 46.3 (C-3), 46.1 (C-2) ppm. ESI-QToF MS (negative mode): m/z [M–H]$^-$: 159.1, [2M–H]$^-$: 319.2 HR-ESI-QToF MS (positive method): m/z calcul. for C$_6$H$_{13}$N$_2$O$_3$ [M+H]$^+$161.0921. found 161.0923.

Preparation of the Compound I.3

(.R,3S,4R) 4-hydroxy, .-acetamido, 3-Pyrrolidine-N-methylacetamide or α-acetamido-(4-hydroxy-pyrrolidin-3-yl)-N-methylacetamide(αR,3S,4R)

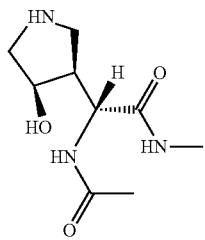

(I.3)

Reducing opening of the N—O bond of the enantiomer of 4 in the presence of molybdenum hexacarbonyl: obtaining the compound 6

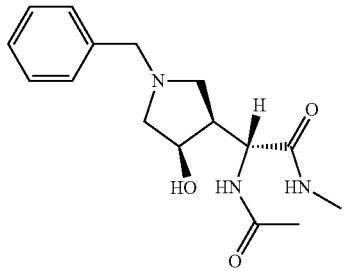

The enantiomer of 4 (116 mg, 0.38 mmol) and molybdenum hexacarbonyl Mo(CO)$_6$ (111 mg, 0.42 mmol, 1.1 equiv.) are introduced into a 50 ml flask equipped with a condenser. The circuit is put under an atmosphere of inert argon. 6 ml of freshly distilled acetonitrile MeCN are added, and then while stirring, 0.5 ml of water (MilliQ quality); the obtained mixture, refluxed by heating (~90° C.) for 3 h, passes from brown to black. After TLC control (CH$_2$Cl$_2$/IPA, 8/2), the reaction medium is concentrated. The obtained suspension is diluted in dichloromethane CH$_2$Cl$_2$ (or tetrahydrofurane THF). The liquid is filtered on a Celite bed (CH$_2$Cl$_2$/MeOH, 9/1 or THF/MeOH 9/1) and then again concentrated. The crude mixture is purified by chromatography on basic alumina Al$_2$O$_3$ (elution gradient CH$_2$Cl$_2$ and then CH$_2$Cl$_2$/MeOH, 8/2) in order to obtain 67 mg of the compound 6 (57%). R$_f$=0.18 (Ace/IPA, 1/1). [α]$_D$=−31.4 (c 0.6, DMSO). $^1$H NMR (400 MHz, CDCl$_3$): δ 7.34-7.23 (m, 5H, CH-ar), 7.10 (d, J=8.0 Hz, 1H, N/Ac), 6.86 (d, J=4.4 Hz, 1H, NHCH$_3$), 4.53 (dd, J=8.0 Hz, J=5.5 Hz, 1H, H-6), 4.45 (td, J=5.5 Hz, J=2.8 Hz, 1H, H-4), 3.66 (d, J=13.0 Hz, 1H, ½NCH$_2$Ph), 3.54 (d, J=13.0 Hz, 1H, ½ NCH$_2$Ph), 2.91 (dd, J=10.3 Hz, J=5.6 Hz, 1H, H-5), 2.76 (d, J=4.8 Hz, 3H, NCH$_3$), 2.64-2.48 (m, 4H, H-5', H-3, H-2, H-2'), 2.01 (s, 3H, NC(O)CH$_3$) ppm.

HR-ESI-QToF MS (positive method): m/z calcul. for C$_{16}$H$_{24}$N$_3$O$_3$ [M+H]$^+$ 306.1812. found 306.1811.

Debenzylation of 6 in the presence of H$_2$ and of Pd(OH)$_2$/C: obtaining the compound I.3

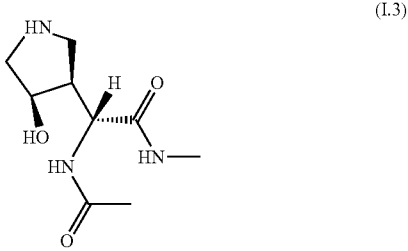

(I.3)

A 25 ml flask containing the compound 6 (40 mg, 0.13 mmol) is subject to 3 vacuum/argon cycles. Under argon 5 ml of ethanol EtOH are added and the obtained mixture is subject to 5 other vacuum/argon cycles. Palladium oxide at 20% on coal Pd(OH)$_2$/C 20% (14 mg, 0.024 mmol, 0.2 equiv.) is added. The flask is then subject to 5 vacuum/argon cycles and finally to 5 vacuum/hydrogen cycles. The reaction mixture is stirred for 1 hour under hydrogen (1 atm) and then filtered on a Celite bed (washing with CH$_2$Cl$_2$ and EtOH). After concentration, the crude mixture is purified by chromatography on a preconditioned C-18 silica column adapted to automated equipment (Combiflash system, elution with water) in order to obtain 23 mg of the compound I.3 (82%). R$_f$=0.31 (n-BuOH/H$_2$O/AcOH, 3/1/1). [α]$_D$=−35.1 (c 0.6, DMSO), $^1$H NMR (400 MHz, D$_2$O): δ 4.42 (t, 1H, J=4.0 Hz; H-4), 4.39-4.24 (m, 1H, H-6), 3.31-3.17 (m, 2H, H-2, H-5), 3.09-2.91 (m, 2H, H-2', H-5'), 2.77 (br s, 3H, NCH$_3$), 2.52-2.34 (m, 1H, H-3), 2.06 (br s, 3H, NC(O)CH$_3$) ppm.

HR-ESI-QToF MS (positive method): m/z calcul. for C$_9$H$_{15}$N$_3$NaO$_3$ [M+Na]$^+$ 236.1006. found 236.1005.

Preparation of the Compound I.4

(αS,3R,4S) 4-hydroxy, .-amino, 3-Pyrrolidine N-methylacetamide or .-amino-(4-hydroxy-pyrrolidin-3-yl)-N-methylacetamide(αS,3R,4S)

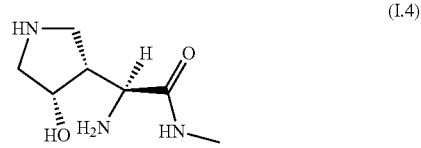

(I.4)

A 50 ml round flask containing the compound 5 (100 mg, 0.38 mmol) is put in a vacuum, and then filled with argon (3 cycles). Still under argon, 10 ml of ethanol EtOH and 6 ml of dichloromethane CH$_2$Cl$_2$ are added and the whole is put under reduced pressure, and then under argon (5 cycles). 100 μl of acetic acid AcOH and 40 mg of palladium hydroxide on coal Pd(OH)$_2$/C 20% (0.076 mmol, O$_2$ equiv.) are introduced. The flask is finally subject to 5 vacuum/argon cycles and then to 5 vacuum/hydrogen cycles. Stirring under hydrogen (1 atm) is maintained for one night, after which TLC shows the complete conversion of 5. The catalyst is separated by filtration on a Celite layer (EtOH/MeOH). After concentration, the crude product is treated by addition of methanol MeOH (2 ml) and of toluene (5 ml), giving the compound I.4 in the form of a precipitate weighing 36.7 mg, i.e. a yield of 55%.

White solid; $R_f$=0.19 (n-BuOH, CH$_3$CO$_2$H, H$_2$O, 3:1:1); [α$^{22}$$_D$]=+ 3.0 (c 0.5, H$_2$O).

$^1$H NMR (D$_2$O, 400 MHz) δ 2.40 (m, 1H, H-3), 2.74 (s, 3H, J$_{gem}$=J$_{2,3}$=11.8 Hz, H-2), 3.23 (dd, 1H, J$_{2',3}$=8.5 Hz, J$_{gem}$=11.6 Hz, H-2'), 3.40 (m, 2H, H-5, H-5') 3.50 (d, 1H, J$_{3,6}$=9.9 Hz, H-6), 4.61 (m, 1H, J$_{3,4}$=3.7 Hz, H-4); COSY actually shows the correlation H-6/H-3, and then H-3/H-2/H-2' and H-4;

$^{13}$C NMR (D$_2$O, 100 MHz) δ 26.07 (NCH$_3$), 45.37 (C-2), 47.29 (C-3), 53.07 (C-6), 53.70 (C-5), 69.31 (C-4), 175.9 (CO);

MS: ESI (positive method): 174.0 [M+H]$^+$, 347.0 [2M+H]$^+$; HRMS Calcul. for C$_7$H$_{15}$N$_3$O$_2$Na$_1$, m/z=196.1056. found: 196.1051 (also visible: 174.1228 [M+H]$^+$; 212.0788 [2M+H]$^+$).

Preparation of the Racemic Compound I.5

(3,4-cis) 4-hydroxy α-N methylamino 3-pyrrolidine acetic acid or (3,4-cis).α-N-methylamino-(4-hydroxy-pyrrolidin-3-yl)acetic acid

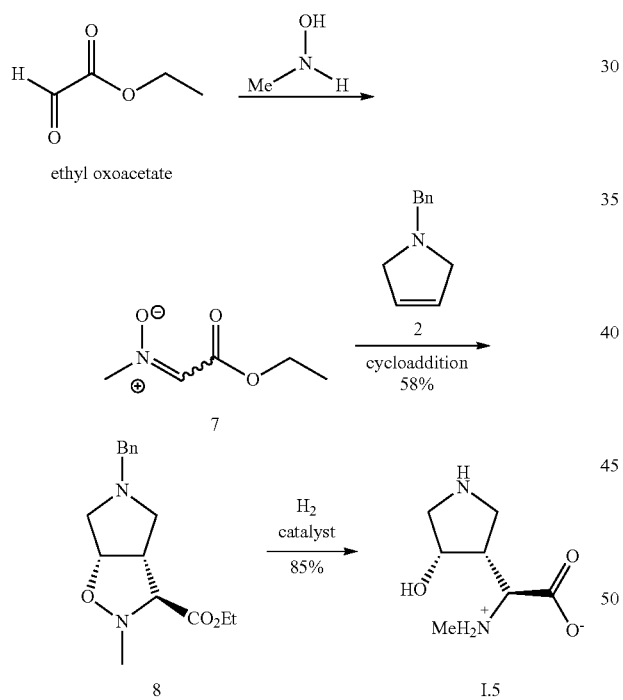

Preparation of the Nitrone 7:

It is compliant with the procedures already described [P. DeShong, C. M. Dicken, R. R. Staib, A. J Freyer, S. W. Weinreb, *J. Org. Chem*, 1982, 47, 4397-4403; P. DeShong, J. M. Leginus, *J. Org. Chem.*, 1984, 49, 3421-3423; Z. Y. Hong, L. Liu, C.-C. Hsu, C.-H. Wong, *Angew. Chem. Int. Ed*, 2006, 45, 7417-7421].

Oxoethyl acetate (also-called ethyl glyoxalate) (330 mg, 3.2 mmol) is dissolved in toluene (7 ml), and then N-methyl-hydroxylamine hydrochloride (270 mg, 3.2 mmol) and NaHCO$_3$ (543 mg, 6.4 mmol) are added and the mixture is stirred for 24 h at room temperature. The reaction mixture is filtered and the solvent evaporated. The nitrone 7 (363 mg, 87%, in a Z/E 3:1 mixture) is directly used in the next step without any additional purification. Aspect: colorless oil. $R_f$=0.5 (petroleum ether/ethyl acetate 4:1), $^1$H NMR (300 MHz, CDCl$_3$): isomer Z: δ 7.23 (q, 1H, $^4$J=0.7 Hz, CH), 4.24 (q, 2H, J=7.1 Hz, O—CH$_2$—CH$_3$), 4.17 (d, 3H, $^4$J=0.7 Hz, CH$_3$—N), 1.31 (t, 3H, J=7.1 Hz, O—CH$_2$—CH$_3$) ppm; isomer E: δ 7.11 (br s, 1H, CH), 4.29 (q, 2H, J=7.1 Hz, O—CH$_2$—CH$_3$), 5.32 (br s, 3H, CH$_3$—N) 1.32 (t, 3H, J=7.1 Hz, O—CH$_2$—CH$_3$) ppm.

Cycloaddition of the nitrone 7 on benzyl-3-pyrroline 2 in order to obtain the heterobicycle 8:

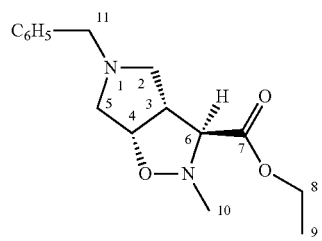

The nitrone 7 (300 mg, 2.29 mmol) and benzyl-3-pyrroline 2 (0.8 ml, 4.20 mmol) are dissolved in toluene (3 ml) and stirred for 1 h at 80° C. with microwave irradiation. TLC (AcOEt/petroleum ether 1/3) shows total transformation of the nitrone. The solvent is then evaporated before purification of the cycloadduct 8 (390 ring, 58%) on a silica column (eluent: AcOEt/toluene 1/4) which removes the more polar compounds also formed. Aspect: colorless oil. $R_f$=0.4 (EtOAc/toluene 1/4). $^1$H NMR (500 MHz, CDCl$_3$): δ 7.35-7.2 (m, 5H, H—Ar), 4.60 (dd, 1H, $^3$J=4.9 Hz, J=7.4 Hz, H-4), 4.20 (q, 2H, $^3$J=7.1 Hz, H-8, H-8'), 3.7 (d, 1H, $^2$J=13.2 Hz, H-11), 3.58 (d, 1H, $^2$J=13.2 Hz, H-11'), 3.24 (q, 1H, $^3$J=7.1 Hz, H-3), 3.16 (br s, 1H, H-6), 3.00 (d, 1H, $^3$J=11 Hz, H-5), 2.94 (d, 1H, $^3$J=9.8 Hz, H-2), 2.78 (s, 3H, NCH$_3$), 2.28 (br s, 1H, H-2'), 2.19 (br s, 1H, H-5'), 1.27 (t, 3H, $^3$J=7.1 Hz, H-9) ppm. $^{13}$C NMR (126 MHz, CDCl$_3$): δ 170.03 (C-7), 138.58, 128.73, 128.41, 127.17 (C—Ar), 81.03 (C-4), 75.48 (C-6), 61.26 (C-8), 59.08 (C-11), 58.77 (C-5), 56.79 (C-2), 52.54 (C-3), 43.85 (NCH$_3$), 14.24 (C-9) ppm. HRMS ESI: m/z calcul. for C$_{16}$H$_{23}$N$_2$O$_3$ [M+H]$^+$: 291.1703. found: 291.1702.

Reduction of the bicycle 8 into (3,4-cis) α-N-methylamino-(4-hydroxy-pyrrolidin-3-yl) acetic acid I.5:

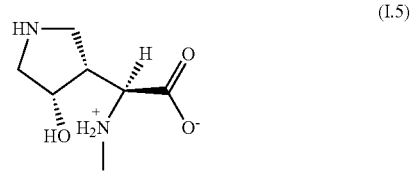

(I.5)

The cycloadduct 8 (150 mg, 517 μmol) is dissolved in a THF/water mixture 1:1 (15 ml). The catalyst 20% Pd(OH)$_2$/C (20 mg) is added, and then the reaction mixture is stirred under an H$_2$ atmosphere at room temperature. These conditions cause debenzylation and the opening of the N—O bond as well as saponification of the ester, which are complete after ~12 h with stirring. The reaction mixture is filtered on celite and then the solvent is evaporated. Purification on a reverse phase column followed by recrystallization from MeOH gives the possibility of obtaining the compound I.5 (80 mg, 85%). Aspect: white crystals; mp 192° C. (MeOH). $^1$H NMR (400 MHz, D$_2$O): δ 4.54 (t, 1H, $^3$J=3.2 Hz, H-4), 3.36 (dd, 1H, $^3$J=3.3 Hz, $^2$J=12.8 Hz, H-5), 3.31 (dd, 1H, $^3$J=0.9 Hz, $^2$J=12.7 Hz, H-5'), 3.26 (dd, 1H, $^3$J=8.5 Hz, 2-=11.6 Hz, H-2), 3.17 (t, 1H, $^2$J=$^3$J=11.7 Hz, H-2'), 3.17 (d, 1H, J=10 Hz, H-6), 2.34 (s, 3H, NCH$_3$), 2.32 (m, 1H, H-3) ppm. $^{13}$C NMR (101 MHz, D$_2$O): δ 178.99 (C-7), 69.41 (C-4), 62.78 (C-6), 53.87 (C-5), 46.04 (C-3), 45.79 (C-2), 33.47 (NCH$_3$) ppm. HRMS CI: m/z calcul. for C$_7$H$_{15}$N$_2$O$_3$ [M+H]$^+$: 175.1078. found: 175.1077.

Preparation of the Racemic Compound I.6

3,4-cis 3-(1,2-diaminoethyl)-4-hydroxy-pyrrolidine)

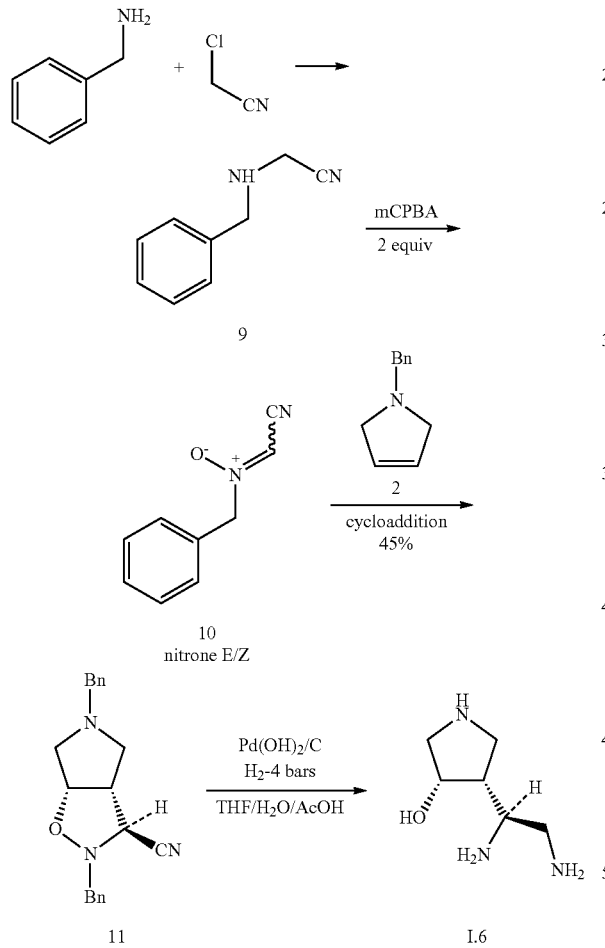

The nitrone was prepared from N-cyanomethylbenzylamine 9 as described by H. Tokuyama, T. Kuboyama, A, Amann, T. Yamashita, T. Fukuyama, *Synthesis* 2000, 1299-1304.

Obtaining N-cyanomethylbenzylamine 9:

To a solution of benzylamine (1 ml, 9.15 mmol) in acetonitrile (50 ml), chloroacetonitrile (870 µl, 13.7 mmol) and K$_2$CO$_3$ (2.53 g, 18.3 mmol) are added under an argon atmosphere. After 15 h of stirring at 60° C., the mixture is filtered on celite and then the filtrate is concentrated. N-cyanomethylbenzylamine 9 (1.03 g, 77%) is purified by a chromatographic column on silica gel (eluent: petroleum ether/ethyl acetate 3:1).

Aspect: colorless oil. R$_f$=0.25 (petroleum ether/ethyl acetate 2:1). $^1$H NMR (300 MHz, CDCl$_3$): δ 7.4-7.25 (m, 5H, H—Ar), 3.94 (s, 2H, CH$_2$—CN), 3.57 (s, 2H, CH$_2$-Ph) ppm. $^{13}$C NMR (75 MHz, CDCl$_3$): δ 138.0, 128.5, 128.3, 127.5, 117.8, 52.2, 36.1 ppm.

Oxidation of N-cyanomethylbenzylamine 9 into cyanonitrone 10:

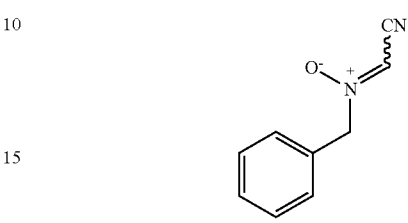

N-cyanomethylbenzylamine 9 (530 mg, 3.62 mmol) is dissolved in anhydrous dichloromethane (20 ml), and then meta-chloroperbenzoic acid (m-CPBA, 2 g, 8 mmol) is added in small portions at 0° C. After 30 min of stirring at 0° C., and then for 1 h at room temperature, the reaction is stopped by adding a 10% Na$_2$S$_2$O$_3$ solution (10 ml), and then a solution saturated with K$_2$CO$_3$ (10 ml). The mixture is stirred for a further 30 min before being extracted three times with dichloromethane. The organic phases are washed with brine and dried with MgSO$_4$. Purification on silica (eluent: petroleum ether/ethyl acetate 4:1) allows the cyanonitrone 10 (550 mg, 95%) to be obtained in two isomeric forms Z and E (Z/E ratio 3:1). Aspect: white crystals. R$_f$(E)=0.7 (petroleum ether/ethyl acetate 3:1); R$_f$(Z)=0.4 (petroleum ether/ethyl acetate 3:1). $^1$H NMR (300 MHz, CDCl$_3$): δ 7.6-7.3 (m, 5H, H—Ar), 6.67 (s, 1H, CH—CN E), 6.57 (s, 1H, CH—CN Z), 5.32 (s, 2H, Ph-CH$_2$ E), 5.01 (s, 2H, Ph-CH$_2$ ppm. $^{13}$C NMR (75 MHz, CDCl$_3$): δ 132-129 (C—Ar), 113.2 (CN, E), 112.4 (CN, 2), 107.5 (CH, E and Z), 71.7 (CH$_2$, 70.1 (CH$_2$, E) ppm.

Cycloaddition of cyanonitrone 10 on 2 in order to obtain the heterobicycle 11:

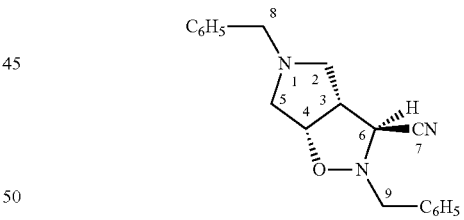

Cyanonitrone 10 (550 mg, 3.44 mmol) and benzyl-3-pyrroline 2 (13 ml, 6.83 mmol) are dissolved in toluene (4 ml) and stirred for 2 h at 80° C. under microwave irradiation (display temperature: 80° C.). The solvent is then evaporated before purification and separation on a silica column (eluent: AcOEt/toluene 1/10) of a regioisomer (60 mg, 6%) in order to obtain the expected racemic cycloadduct 11 (500 mg, 45%). Aspect: yellow oil. R$_f$=0.4 (EtOAc/toluene 1/4). $^1$H NMR (400 MHz, 60° C., toluene-D$_8$): δ 7.3-7.0 (m, 10H), 4.28 (ddd, 1H, J=3.4 Hz, J=6.0 Hz, J=7.5 Hz, H-4), 4.17 (d, 1H, J=13.4 Hz, H-9), 3.81 (d, 1H, J=13.4 Hz, H-9'), 3.30 (d, 1H, J=13.1 Hz, H-8), 3.23 (d, 1H, J=13.1 Hz, H-8'), 3.06 (d, 1H, J=3.6 Hz, H-6), 2.79 (ddd, 1H, J=3.8 Hz, J=7.9 Hz, J=11.6 Hz, H-3), 2.47 (ddd, 1H, J=3.0 Hz, J=10.0 Hz, H-5), 2.24 (br m, 1H, H-5'), 2.16 (br m, 1H, H-2), 2.07 (br m, 1H, H-2') ppm.

$^{13}$C NMR (100 MHz, 60° C., toluene-D$_8$): δ 139.3, 136.7, 129.7, 129.7, 129.0, 129.0, 128.8, 128.8, 128.8, 128.8, 128.1, 127.6, 116.5 (C-7), 81.4 C-4), 59.5 (C-8), 59.3 (3C, C-5, C-6, C-9), 57.0 (C-2), 53.0 (C-3) ppm. HRMS: m/z calcul. for C$_{20}$H$_{22}$N$_3$O [M+H]$^+$: 320.1757. found: 320.1767.

Reduction of the bicycle 11 into 3,4-cis 3-(1,2-diaminoethyl)-4-hydroxy-pyrrolidine, I.6:

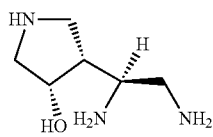

(I.6)

The cycloadduct 11 (40 mg, 125 μmol) is dissolved in a THF/water/AcOH 10:10:1 mixture (3 ml). The catalyst 20% Pd(OH)$_2$/C (10 mg) is added to the medium, and then the mixture is stirred under 4 bars of H$_2$ at room temperature for about 40 h. A test with TLC (eluent nBuOH-water-AcOH 3:1:1) shows complete conversion of the initial product. The medium is filtered on celite and then the solvent is evaporated (23 mg). Analysis by mass spectrometry shows an ion in high majority corresponding to the expected polyamine I.6 and another one for a minor product still benzylated, $^{13}$C NMR confirms the existence of both of these products in a proportion from 1:3 to 1:4. $^{13}$C NMR (75 MHz, D$_2$O): δ 69.20 (C-4), 53.73 (C-5), 48.14 (C-6), 45.72 (C-3), 45.09 (C-2), 42.52 (C-7) ppm. HRMS (ESL positive method; infusion solvent: water/MeOH 1:1): m/z calcul. for C$_6$H$_{16}$N$_3$O [M+H]$^+$ 146.1288. found: 146.1281.

II. Biological Activities

II.1 Evaluation of the Modulating Activity of the Extracellular Glutamate and Aspartate Levels One of the widespread methodological approaches, both in academic laboratories and in industrial laboratories, and used for following the extracellular concentrations of glutamate (Glu) and of aspartate (Asp) before, during and after administration of pharmacological agents targeting their receptors is intracerebral microdialysis [7]. This type of test was therefore used, in order to track the in vivo effects of the molecules according to the invention as compared with those of kainic acid, for which the synthesized molecules are structural analogues (substituted pyrrolidines).

Microdialysis Probes

Concentric microdialysis probes with a regenerated cellulose membrane (Spectra/Por hollow fiber; molecular cut off 6,000 Da, 225 μm in external diameter, a length of 3 mm, Spectrum Medical Industries, Los Angeles, Calif., USA) and tubings in molten silica (40 μm i.d×105 μm o.d., Polymicro Technology, Phoenix, Ariz., USA) were manufactured according to a design already published (Bert et al 1996, [26]). They were perfused with a flow rate of 1 μl/min with artificial cerebrospinal fluid or CSF (145.0 mM NaCl; 21 mM KCl; 1.0 mM MgCl$_2$; 1.2 mM CaCl$_2$; 0.45 mM NaH$_2$PO$_4$; 1.55 mM Na$_2$HPO$_4$; pH 7.4) by means of a Harvard pump (Model 22, South Natick, Mass., USA).

Implantation of Microdialysis Probes.

The in vivo microdialysis experiments were conducted on male rats of the Wistar strain with an average weight of about 300 g, (provider: Charles River, L'Arbresle, France) anesthetized with urethane (a dose of 1.4 g/kg via an i.p, route, provider: Sigma-Aldrich, St. Louis, Mo., USA). The probes were implanted dorso lateral striatum according to the following stereotaxic coordinates relatively to the bregma: antero-posteriority 0 mm, laterality +15 mm, depth +605 mm under the cortical surface. The dialysates (samples) were collected from the beginning of the 4$^{th}$ hour after implantation of the probe. The samples were taken every 5 minutes in PCR tubes of 200 μl (Axygene, Union City, Calif., USA) and immediately frozen at −20° C. The samples were analyzed subsequently in order to determine the glutamate and aspartate contents. The pharmacological agents and the compounds according to the invention were administered in situ by reverse microdialysis by changing the perfusion at the inlet of the probe of the CSF without any pharmacological agent to the one containing the pharmacological agent(s) (Bert et al., 2002 [27]; Parrot et al 2003 [28]).

Capillary Electrophoresis (CE)

CE analyses were carried out with a P/ACE MDQ system (Beckman-Coulter, Fullerton, Calif., USA) equipped with an external detector LIF ZETALIF (Picometrics, Toulouse, France). Detection was achieved by fluorescence at a wavelength of 442 nm and generated with a He—Cd laser Omnichrome (Chino, Calif., USA). The emission intensity was collected at 490 nm. Before analysis, the samples were derived with naphthalene-2,3-dicarboxaldehyde with cyanide ions as a nucleophilic agent (pH 8.7; borate buffer 500 mM). The separations were conducted in a capillary of molten silica with an internal diameter of 50 cm and an outer diameter of 375 μm with a length of 63 cm, with a useful length of 52 cm (Polymicro Technology) by using the procedure entirely detailed and validated earlier (Sauvinet et al., 2003 [29] Bert et al., 2002 (271). The Glu and Asp concentrations measured in striatum samples were above detection limits and were determined by interpolation by means of standard ranges.

Reagents

All the reagents of the neurochemical study (except for the compound according to the invention) were purchased from Sigma-Aldrich (St Louis, Mo., USA). The mother-solutions of the synthesized molecules, of the kainate (KA, agonist of the KA receptors for glutamate), CNQX, 6-cyano-7-nitroquinoxaline-2,3(1H,4H)-dione (CAS-No. 115066-14-3, antagonist of KA receptors), from Glu and Asp were aliquoted to 1 or 0.1 mM and stored at −30° C. After their administration, the tested pharmacological agents were diluted in artificial CSF.

Analyses of the Data

The final data were expressed in % of the average of four values preceding administration of the KA.

Results and Discussion

Four molecules according to the invention were tested in vivo on the brain (brain structure: striatum) of anesthetized entire animals. Their effects were compared with that of kainate (KA), an agonist of the glutamate receptors of the KA type. The results are shown in the appended FIGS. 1A, 1B, 2A, 2B and 3.

Figure 3:
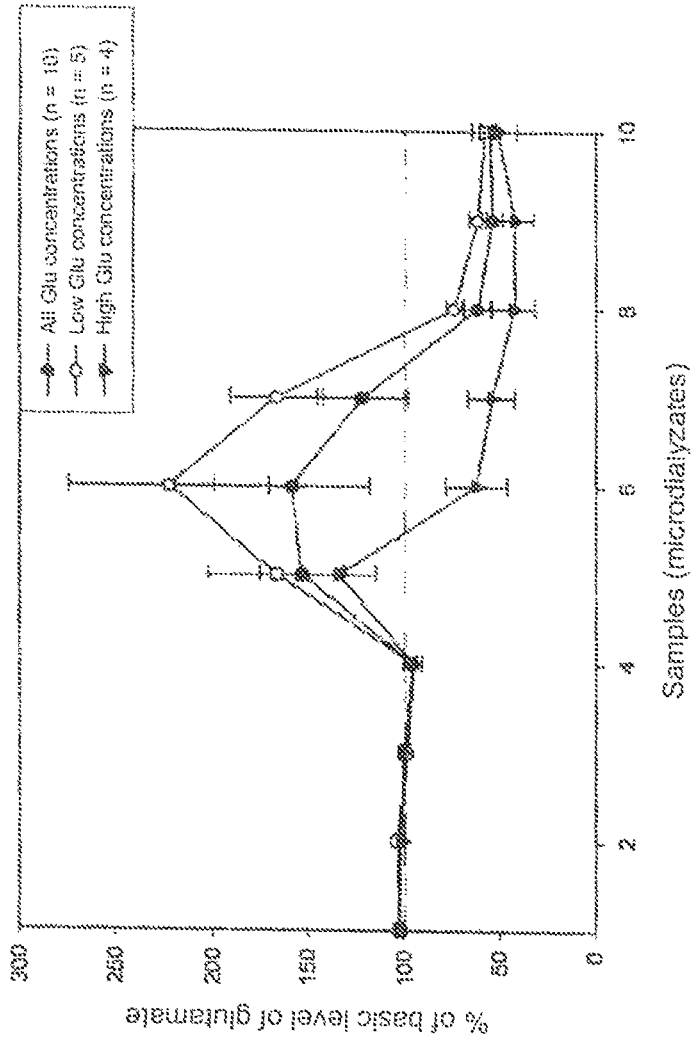
FIG. 3 shows the effects of the kainate (KA) tested in vivo on the brain (brain structure: striatum) of anesthetized entire animals, versus the initial endogenous glutamate concentration.

The obtained results show that the response to KA was variable from one subject to another. The glutamate and aspartate levels were affected by the administration of KA at 1 mmol/L. This systematic control thus allowed us to check the reactivity of striatum neurones towards KA receptors. FIGS. 1A and 18 compare the effects of the molecules I.1 and I.2 with and without kainate (KA) respectively, FIGS. 2A and 2B compare the effects of I.3 and I.4 with and without kainate (KA) respectively, and FIG. 3 shows the effects of the kainate (KA) versus the initial endogenous glutamate concentration.

Compound I.1 at 1 mmol/L (n=2): The compound I.1 induces effects similar to KA which may be attenuated since the Glu and Asp levels tend to return to the basal levels.

Compound I.2 at 1 mmol/L (n=2): The compound I.2 induces a reduction in the Glu and Asp levels (a similar effect to those of kainate), and the CNQX seems to partly attenuate its effects significantly since the Asp levels are increased subsequent to its co-administration with the compound I.2.

Compound I.3 at 1 mmol/L (n=2): The compound I.3 induces an effect similar to that of kainate, and the CNQX seems to partly attenuate its effects significantly since the Asp levels are increased subsequent to its co-administration with the compound I.3 (n=1).

Compound I.4 at 1 mmol/L (n=1): The compound I.4 induces a reduction in the Glu and Asp levels (effect similar to those of kainate), and the CNQX seems to partly attenuate its effects significantly since the Asp levels are increased subsequent to co-administration with the compound I.4 (n=1).

TABLE 1 summary of the preliminary results

|  | Compound I.1 | Compound I.2 | Compound I.3 | Compound I.4 |
|---|---|---|---|---|
| Effect on Glu and/or Asp | Yes | Yes | yes | yes |
| Action through the KA receptors | not determined | yes for Asp | not determined | yes for Asp |
| Pharmacological potentiality for modulating the Glu system | Yes | Yes | yes | yes |

The results show that the compounds according to the invention, which are structural analogues of kainic acid, act on the extracellular glutamate and aspartate levels.

The compounds according to the invention, and in particular, the compounds I.1, I.2, I.3 and I.4 have inhibitory actions on the glutamate when the glutamate levels are high and consequently are good candidates for treating, and in particular for treating human beings, with pathologies like Parkinson's disease, epilepsy, addictive disorders or ischemia [2-5; 7].

II.2 Determination of the Target Receptors

In order to determine the target receptors of the compounds according to the invention, experiments of specific binding inhibition were conducted in vitro. Pharmacology in vitro: tests of specific bindings.

Sixty receptors were tested in the study according to standardized methods by using their specific radioligand as reported earlier [30-88].

The results may be expressed as a % of the specific control bond [(measured specific bond/control specific bond)×100] and as a % of inhibition of the specific control bond [100−(measured specific bond/control specific bond)×100] obtained in the presence of one of the two tested compounds (I.2 and I.4).

These experiments (Table 2 hereafter) have shown that the compounds I.2 and I.4 modify the specific binding of a control agonist of the receptors of type 1 to endocannabinoids (CB-1) (according to the test described in reference [83]).

TABLE 2

Values of the % of inhibition of the control specific bond at 10 µM (n = 2) for the tested compounds.

| % of inhibition of the control specific binding at 10 µM | Compound I.2 | Compound I.4 |
|---|---|---|
| CB1 towards its agonistic ligand | +29% | +29% |

The % of inhibition correspond to a significant effect according to an analysis on 60 target receptors (n=2) with a representation of the 'box and whisker' type carried out for each compound.

These results, as well as the neurochemical results, which show that the compounds I.2 and I.4 cause a reduction in the cerebral extracellular glutamate levels are consistent with neuropharmacological literature. Indeed, an agonist of the CB-1 receptors, such as WIN 55, 212-2, also induces a reduction in the glutamate levels in the striatum of ex vivo and in vivo preparations [89-90], whereas CB-1 antagonists, such as rimonabant or SR-141716A, cause an increase or do not affect the extracellular glutamate levels [91-92]. The compounds I.2 and I.4 induce effects close to those observed with cannabinoidergic agents.

The CB-1 receptors are involved in addiction [93] and schizophrenia [94], depression and pain [95], neurodegenerative diseases [96], but also in the control of food intake [97] and cardiac and digestive functions [98]. Therefore, the compounds according to the invention, and in particular the compounds I.2 and I.4, are good candidates for treating such pathologies.

II.3 Passing Through the Blood-Brain Barrier

A study was conducted with the BIP platform (Centre de Recherche en Neurosciences de Lyon, Lyons, France) for comparing the inflow of four compounds of interest through the cerebrospinal liquid/blood barrier. The study was carried out with an in vitro model of the choroidal epithelium restoring this interface. Choroidal cells were exposed by their basolateral pole to the compounds at a concentration of 150 µm for 60 minutes. The permeability of the cell monolayers to saccharose was analyzed in terms of these transfers, in order to detect possible toxicity of the compounds.

Methods

Primary Cultivation of Choroidal Epithelial Cells

The epithelial cells are isolated from the choroidal plexus of a lateral ventricle taken on newly born rats as described earlier [99-100]. The cells are sown on microporous supports (Transwell PC, pore size 0.4 µm, surface area 033 cm$^2$, diameter 6.5 mm), and cultivated in DMEM-F12 (1:1) supplemented with 10% FCS, 2 mM glutamine and 50 µg/ml gentamycin, as well as with various growth factors [99]. The medium is renewed every two days until the day of experiment.

Measurement of Permeability

The transfer measurements were conducted under kinetic conditions (3 phases), with stirring (200 rpm), at 37° C., in a Ringer-Hepes buffer (RH). The volumes used in both compartments during the transfer are adjusted so as to minimize any hydrostatic pressure effect. The inserts are rinsed in RH before initiating the permeability study. For each compound, the transfer is carried out in parallel on three laminin inserts (without any cell) and three inserts with a cell monolayer.

Inflow of the Compounds I.1, I.2, I.3 and I.4

Inflow measurements (from blood to the cerebrospinal fluid) were conducted during a kinetic study [101] (20 min periods) for the four compounds of interest. Briefly, the compound of interest, diluted to 150 µm in RH is placed in the lower compartment of a multi-well cultivation plate, which reproduces the blood compartment. Transfer is initiated by placing a culture insert containing RH in the upper compartment, which corresponds to the cerebrospinal fluid. At regular intervals, an aliquot of the upper medium is taken and replaced with an equivalent volume of preheated RH at 37° C. At the end of the transfer, the lower medium is also sampled for assaying the residual compound. The samples taken are analyzed by high performance liquid chromatography (HPLC) on an LC10 Shimadzu system chain (Duisburg, Germany), equipped with a spectrophotometric detector.

Permeability of the Saccharose

At the end of the transfer of the compounds of interest, [$^{14}$C]-saccharose is added as an aliquot into the upper compartment of the inserts. At regular intervals, the inserts are transferred into neighboring wells containing preheated RH at 37° C. The media sampled in the wells and in the inserts at the end of the transfer of saccharose are analyzed by liquid scintillator counting in a β Canberra Packard TRI-GARB 1600TR counter.

Calculation of the Permeability Coefficients

The calculation method is described in detail in [101]. Briefly, the successive samples from the acceptor compartment during transfer kinetics give the possibility of plotting clearance curves. The slope of these curves representing the clearance rate may be assimilated to the product of permeability×surface area of the compound (PS in $\mu l \cdot min^{-1}$ per filter).

The permeability coefficient of the cell monolayer Pe (in $cm \cdot min^{-1}$) is calculated from the PS determined on laminin filters and filters with cells and by taking into account the exchange surface area.

Method for Assaying the Compounds I.1 and I.2

An assaying technique by HPLC preceded by a step for deriving primary amines was applied from an existing method [102] for both compounds I.1 and I.2. The derivation reaction is carried out with OPA (o-phthaldialdehyde, 10 mg), 200 μl of methanol, 1.8 ml of 200 mM borate buffer at pH of 9.5 and 10 μl of 2-β-mercaptoethanol. The sample volume to volume reaction is carried out for 2 min at room temperature. The derivative is stable for 30 to 40 min.

Analytical conditions: RP-18 column, 15 cm, 5 μm. Mobile phase: A: 90/10 (potassium phosphate buffer 50 mM pH6/methanol); B: 100% methanol. Detection: 340 nm. Flow rate: 1 ml/min. Injection volume: 20 μl. Gradient used min (A:B): 0-5 (83:17); 6-11 (35:65); 12-17 (83:17).

Method for Assaying the Compounds I.3 and I.4

An assaying technique by HPLC preceded by a step for deriving secondary amines with Fmoc (fluorenylmethyloxycarbonyl chloride; at 5 g/l in acetonitrile was developed for both compounds I.3 and I.4. The derivation reaction was conducted for 30 min at room temperature in borate buffer 208 mM at pH 9.5 (25 μl of sample+20 μl of borate buffer+5 μl of a 5 g/L solution of Fmoc). The derivative formed is stable for 2 h.

Analytical conditions: RP-18 column, 15 cm, 5 μm. Mobile phase: A: 90/10 (sodium acetate buffer 50 mM pH 4.2/acetonitrile); B: 100% acetonitrile. Detection: 230 nm. Flow rate: 1 ml/min. Injection volume: 20 μl. Gradient used for the molecule I.3 min (A:B): 0 (75:25); 8.5 (67:33); 9.5-20 (20:80); 21-26 (75:25). Gradient used for the molecule I.4 min (A:B): 0 (65:35); 18 (40:60); 19-29 (20:80); 30-35 (35:35).

The experiments conducted showed in vitro that the compounds according to the invention were able to pass the blood-brain barrier.

Moreover, given a low penetration rate ($\leq 0.3 \times 10^{-3}$ cm/min) of the peripheral blood compartment towards the brain compartment for the four tested compounds (I.1, I.2, I.3 and I.4), the compounds according to the invention were able to induce peripheral effects with very few central secondary effects.

This strongly suggests a possible pharmacological use of such compounds for acting on different organs and peripheral tissues, in the treatment of cancers [103], obesity [104], musculo-skeletal disorders [105], cardiovascular diseases and diseases of the digestive tract [98], in addition to the treatments mentioned earlier.

CITED REFERENCES

1. Formum F, (1984). Glutamate: a neurotransmitter in mammalian brain. J. Neurochem, 42, 1-11.
2. Farber N B, Newcomer J W, Olney J W, (1998). The glutamate synapse in neuropsychiatric disorders. Focus on schizophrenia and Alzheimer's disease. Prog Brain Res, 116, 421-437.
3. Avoli M, Louvel J, Pumain R, Kohling R, (2005). Cellular and molecular mechanisms of epilepsy in the human brain. Prog Neurobiol, 77, 166-200.
4. Javitt D C, (2004). Glutamate as a therapeutic target in psychiatric disorders. Mol Psychiatry, 9, 984-997, 979.
5. Gubellini P, Pisani A, Centonze D, Bemardi G, Calabresi P, (2004). Metabotropic glutamate receptors and striatal synaptic plasticity: Implications for neurological diseases. Prog Neurobiol, 74, 271-300.
6. Bevan M D, Atherton J F, Baufreton J, (2006). Cellular principles underlying normal and pathological activity in the subthalamic nucleus. Curr Opin Neurobiol, 16, 621-628.
7. Parrot S, Renaud B, Zimmer L, Denoroy L, (2011) Monitoring neurotransmitter amino acids by microdialysis: pharmacodynamics applications. In: "Applications of Microdialysis in Pharmaceutical Science" (Ed: T-H Tsai). Wiley.
8. C. Berini, N. Pelloux-Léon, F. Minassian, J.-N. Denis Org. Biomol. Chem. 2009, 7, 4512-16
9. J. E. Baldwin, R. M. Adlington, D. W. Collins, C. J. Schofield Tetrahedron 1990, 46, 4733-4748
10. S. Horli, H. Fukase, E. Higashide, M. Yoneda, H. Nishida, H. Sakai, A. Hirota, I. Isogai J. Antibiot. 1985, 38, 302
11. Zanobini, A.; Gensini, M.; Magull, J.; Vidovic, D.; Kozhushkov, S. I.; Brandi, A.; de Meijere, A. Eur. J. Org. Chem. 2004, 4158-66
12. Thèse de J. A. Stanko, Duke University, USA, 2009
13. U. Chiacchlo, A. Corsaro, D. Iannazzo, A. Piperno, V. Pistarà, A. Rescifina, R. Romeo, G. Sindona, G. Romeo, Tetrahedron Asymm. 2003, 14, 2717-2723.
14. L. Weselinski, E. Slyk, J. Jurczak Tetrahedron Lett. 2011, 25, 381-384.
15. U. Chiacchio, A. Corsaro, V. Pistarà, A. Rescifina, D. Iannazzo, A. Piperno, G. Romeo, R. Romeo, G. Grassi Eur. J. Org. Chem. 2002, 1206-1212.
16. U. Chiacchlo, F. Genovese, D. Iannazzo, V. Ubrando, P. Merino, A. Rescifina, R. Romeo, A. Procopio, G. Romeo, Tetrahedron 2004, 60, 441-448.
17. D. Iannazzo, C. Carnovale, S. V. Giofrè, R. Ettari, G. Romeo, R. Romeo, G. Lanza, U. Chiacchio Synlett 2011, 245-248.
18. U. Chiacchio, A. Corsaro, G. Gumina, A. Rescifina, D. Iannazzo, A. Piperno, G. Romeo, R. Romeo J. Org. Chem. 1999, 64, 9321-9327.
19. K. Kasahara, H. Iida, C. Kibayashi J. Org. Chem. 1989, 54, 2225-2233.

20. V. Ondrus, M. Orsag, L. Fisera, N. Pronayova, Tetrahedron 1999, 55, 10425-10436.
21. N. Morita, K. Fukul, J. Irikuchi, H. Sato, Y. Takano, I. Okamoto, H. Ishibashi, O. Tamura J. Org. Chem. 2008, 73, 7164-7174
22. O. Tamura, N. Morita, Y. Takano, K. Fukul, I. Okamoto, X. Huang, Y. Tsutsumi, H. Ishibashi, Synlett 2007, 658-660.
23. M. Benitifa, S. Vidal, D. Gueyrard, P. G. Goekjian, M. Msaddek, J.-P. Praly, *Tetrahedron Lett.* 2006, 47, 6143-6147
24. Altenbach, H.-J.; Kottenhahn, M.; Vogt, A.; Matthäus, M.; Grundler, A.; Hahn, M. a) DE 19533617 A1, 1997 and b) U.S. Pat. No. 6,018,050, 2000
25. Vogt, A.; Altenbach, H.-J.; Kirschbaum, M.; Hahn, M. G.; Matthäus, M. S. P.; Hermann, A. R. a) EP 976721, 2000; b) Chem. Abstr. 2000, 132, 108296j.
26. Bert L, Robert F, Denoroy L, Stoppini L, Renaud B. *J. Chromatogr. A*, 1996, 755, 99-111.
27. Bert L, Parrot S, Robert F, Desvignes C, Denoroy L, Suaud-Chagny M F, Renaud B. *Neuropharmacology*, 2002, 43, 825-835.
28. Parrot S, Bert L, Mouly-Badina L, Sauvinet V, Colussi-Mas J, Lambás-Señas L, Robert F, Bouilloux J P, Suaud-Chagny M F, Denoroy L, Renaud B. *Cell Mol. Neurobiol.* 2003, 23, 793-804.
29. Sauvinet V, Parrot S, Benturqula N, Bravo-Moratón E, Renaud B, Denoroy L. *Electrophoresis* 2003, 24, 3187-3196.
30. Aharony, D. et al. (1993), Mol. Pharmacol., 44: 356-363.
31. Ardat, A. et al. (1997), Mol. Pharmacol., 51: 816-824.
32. Bloomquist, B. T. et al. (1998), Biochem. Biophys. Res. Commun., 243: 474-479.
33. Bonhaus, D. W. et al. (1995), Brit. J. Pharmacol., 115: 622-628.
34. Brown, G. B. (1986), J. Neurosci., 6: 2064-2070.
35. Brown, P. J. et al. (1990), J. Biol. Chem., 265: 17995-18004.
36. Buchan, K. W. et al. (1994), Brit. J. Pharmacol., 112: 1251-1257.
37. Couvineau, A. et al. (1985), Biochem. J., 231: 139-143.
38. Dorje, F. et al. (1991), J. Pharmacol. Exp. Ther., 256: 727-733.
39. Fuhlendorff, J. et al. (1990), Proc. Natl. Acad. Sci. U.S.A., 87: 182-186.
40. Grandy, D. K. et al. (1989), Proc. Natl. Acad. Sci. U.S.A., 86:9762-9766.
41. Greengrass, P. and Bremner, R. (1979), Eur. J. Pharmacol., 55:323-326.
42. Hope, A. G. et al. (1996), Brit. J. Pharmacol., 118: 1237-1245.
43. Hoyer, D. et al. (1985), Eur. J. Pharmacol., 118: 1-12.
44. Hugues, M. et al. (1982), J. Biol. Chem., 257: 2762-2769.
45. Lewin, A. H. et al. (1989), Mol. Pharmacol., 35: 189-194.
46. Luthin, D. R. et al. (1995), Mol. Pharmacol., 47: 307-313.
47. Monaghan, D. T. and Cotman, C. W. (1982), Brain Res., 252:91-100.
48. Monsma, F. J. et al. (1993), Mol. Pharmacol., 43: 320-327.
49. Mulheron, J. G. et al. (1994), J. Biol. Chem., 269: 12954-12962.
50. Murphy, D. E. et al. (1987), Neurochem. Res., 12: 775-781.
51. Neote, K. et al. (1993), Cell, 72: 415-425.
52. Pacholczyk, T. et al. (1991), Nature, 350: 350-354.
53. Pristupa, Z. B. et al. (1994), Mol. Pharmacol., 45: 125-135.
54. Rees, S. et al. (1994), FEBS Lett., 355: 242-246.
55. Reynolds, I. J. et al. (1986), J. Pharmacol. Exp. Ther., 237:731-738.
56. Salvatore, C. A. et al. (1993), Proc. Natl. Acad. Sci. U.S.A., 90:10365-10369.
57. Schioth, H. B. et al. (1997), Neuropeptides, 31: 565-571.
58. Shen, Y. et al. (1993), J. Biol. Chem., 268: 18200-18204.
59. Baron, B. M. et al. (1996), J. Pharmacol. Exp. Ther., 279: 62-68.
60. Sills, M. A. et al. (1991), Eur. J. Pharmacol., 192: 19-24.
61. Sorensen, R. G. and Blaustein, M. P. (1989), Mol. Pharmacol., 36:689-698.
62. Speth, R. C. et al. (1979), Life Sci., 24: 351-358.
63. Townsend-Nicholson, A. and Schofield, P. R. (1994), J. Biol. Chem., 269: 2373-2376.
64. Tsuji, A. et al. (1988), Antimicrob. Agents Chemother., 32:190-194.
65. Uhlen, S, and Wikberg, J. E. (1991), Pharmacol. Toxicol., 69:341-350; 257.
66. Vignon, J. et al. (1986), Brain Res., 378: 133-141.
67. Vita, N. et al. (1993), FEBS Lett., 317: 139-142.
68. Wang, J. B. et al. (1994), FEBS Lett., 338: 217-222.
69. White, J. R. et al. (1998), J. Biol. Chem., 273: 10095-10098.
70. Zhou, Q. Y. et al. (1990), Nature, 347: 76-80.
71. Tahara, A. et al. (1998), Brit. J. Pharmacol., 125: 1463-1470.
72. Pruneau, D. et al. (1998), Brit. J. Pharmacol., 125: 365-372.
73. Wieland, H. A. et al. (1995), J. Pharmacol. Exp. Ther., 275:143-149.
74. Smit, M. J. et al. (1996), Brit. J. Pharmacol., 117: 1071-1080.
75. Simonin, F. et al. (1994), Mol. Pharmacol., 46: 1015-1021.
76. Leurs, R. et al. (1994), Brit. J. Pharmacol., 112: 847-854.
77. Peralta, E. G. et al. (1987), Embo. J., 6: 3923-3929.
78. Levin, M. C. et al. (2002), J. Biol. Chem., 277: 30429-30435.
79. Bignon, E. et al. (1999), J. Pharmacol. Exp. Ther. 289: 742-751.
80. Tatsumi, M. et al. (1999), Eur. J. Pharmacol., 368: 277-283.
81. Choi, D. S. et al. (1994), FEBS Lett., 352: 393-399.
82. Witt-Enderby, P. A. and Dubocovich, M. L. (1996), Mol. Pharmacol., 50: 166-174.
83. Rinaldi-Carmona, M. et al. (1996), J. Pharmacol. Exp. Ther., 278:871-878.
84. Sarau, H. M. et al. (1997), J. Pharmacol. Exp. Ther., 281:1303-1311.
85. Meng, F. et al. (1993), Proc. Natl. Acad. Sci. U.S.A., 90:9954-9958.
86. Le, M. T. et al. (2005), Eur. J. Pharmacol., 513: 35-45.
87. Abramovitz, M. et al. (2000), Biochem. Biophys. Acta., 1483:285-293.
88. Joseph, S. S. et al. (2004), Naun.-Sch. Arch. Pharm., 369:525-532.
89. Morgese M G et al. (2009) Neurochemical changes in the striatum of dyskinetic rats after administration of the cannabinoid agonist WIN55, 212-2. Neurochem Int., 54(1): 56-64.
90. Polissidis A. et al. (2013) Int J Neuropsychopharmacol., 16(2):393-403.
91. García-Arencibia M et al., (2008) Neurosci Lett. 438(1): 10-3.

92. Berger C et al., (2004) J Neurochem. 88(5):1159-67.
93. Leweke et al (2012) Translational Psychiatry, 2, e94.
94. Lacrosse and Olive (2013) Neuropeptide Systems and Schizophrenia. CNS NeurolDisord Drug Targets, [Epub ahead of print]
95. Adam et al., (2012) Bioorganic & Medicinal Chemistry Letters. 22:2932-2937.
96. Pintor A et al., (2006) Neuropharmacology. 51(5):1004-12.
97. Kirilly et al (2012) Acta Physiol., 1-20.
98. Thakur et al (2009) Expert Opin. Ther Patents, 19(12): 1647-1673.
99. Strazlelle N, et al. J. Neurosci. 1999 Aug. 1; 19(15):6275-89.
100. Strazielle N, et al. AIDS. 2003 Jul. 4; 17(10):1473-85.
101. Strazielle N, et al. Methods Mol. Med. 2003; 89:291-304.
102. Teerlink T, et al. Anal Biochem. 2002 Apr. 15; 303(2): 131-7.
103. Hermanson and Mamett (2011) Cancer Metastasis Rev., 30:599-612.
104. Alen et al (2012) Vitam. Horm., 92:165-96.
105. Robert W. Cowan, et al. Frontiers in Endocrinology (2012), July, Vol. 3 Article 89, doi: 10.3389/fendo.2012.00089.

The invention claimed is:

1. Pyrrolidine derivatives of formula (I):

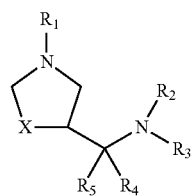

(I)

wherein:
   $R_1$ represents a hydrogen atom, a ($C_1$-$C_6$)alkyl or C(O)($C_1$-$C_6$)alkyl group,
   $R_2$ and $R_3$, either identical or different, each represent independently of each other, a hydrogen atom or a ($C_1$-$C_6$)alkyl group; or else $R_2$=H and $R_3$=C(O)($C_1$-$C_6$)alkyl,
   $R_4$ represents —COOH, —CN, —COOR$_a$, —C(=NOH)NH$_2$, —CH$_2$NH$_2$, —CH$_2$OH, —C(O)NH$_2$, —C(O)NHR$_a$ or —COSR$_a$, with R$_a$ which represents a ($C_1$-$C_6$)alkyl group, or else R$_4$ represents a tetrazole or 1,2,4-oxadiazole group,
   $R_5$ represents a hydrogen atom or a ($C_1$-$C_6$)alkyl group,
   X represents —C(O)— or —CHR$_b$—, with R$_b$ which represents —OR$_c$ or —OC(O)R$_c$, R$_c$ representing a hydrogen atom or a ($C_1$-$C_6$)alkyl group,
optionally in a zwitterionic form,
as a pure optical isomer, or a mixture of optical isomers in any proportions, or in a form enriched with an optical isomer, as well as their pharmaceutically acceptable salts, solvates or hydrates.

2. The pyrrolidine derivatives according to claim 1 characterized in that X represents —CHR$_b$—, with R$_b$ as defined in claim 1.

3. The pyrrolidine derivatives according to claim 1 characterized in that it fits the formula (Ia):

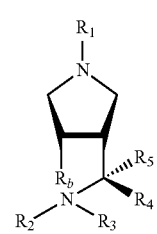

(Ia)

wherein $R_1$, $R_2$, $R_3$, $R_4$, $R_5$ and $R_b$ are such as defined in claim 1, as well as their pharmaceutically acceptable salts, solvates or hydrates.

4. The pyrrolidine derivatives according to claim 1 characterized in that it fits the formula (Ib):

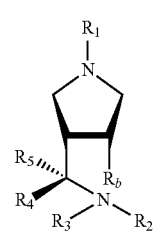

(Ib)

wherein $R_1$, $R_2$, $R_3$, $R_4$, $R_5$ and $R_b$ are as defined in claim 1, as well as their pharmaceutically acceptable salts, solvates or hydrates.

5. The pyrrolidine derivatives according to claim 2, characterized in that R$_b$=OH.

6. The pyrrolidine derivatives according to claim 1, characterized in that R$_1$ is a hydrogen atom.

7. The pyrrolidine derivatives according to claim 1, characterized in that R$_2$=H and R$_3$ represents a hydrogen atom or a methyl or —C(O)CH$_3$ group.

8. The pyrrolidine derivatives according to claim 1, characterized in that R$_4$ represents —COOH, —C(O)NHCH$_3$ or —CH$_2$NH$_2$.

9. The pyrrolidine derivatives according to claim 1, characterized in that R$_5$ is a hydrogen atom.

10. The pyrrolidine derivatives according to claim 1, characterized in that it appears in a salified or zwitterionic form including a quaternary ammonium.

11. The pyrrolidine derivatives according to claim 1 selected from:
   (αS,3R,4S)α-amino-(4-hydroxy-pyrrolidin-3-yl)acetic acid, compound (I.1)

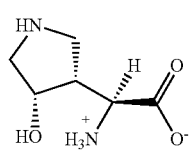

(I.1)

(αR,3S,4R)α-amino-(4-hydroxy-pyrrolidin-3-yl)acetic acid, compound (I.2)

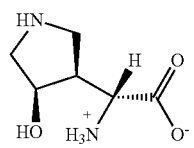

(αR,3S,4R)α-acetamido-(4-hydroxy-pyrrolidin-3-yl)-N-methylacetamide, compound (I.3)

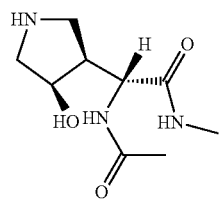

(αS,3R,4S)α-amino-(4-hydroxy-pyrrolidin-3-yl)-N-methylacetamide, compound (I.4)

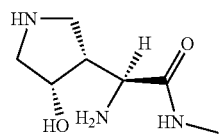

3,4-cis α-N-methylamino-(4-hydroxy-pyrrolidin-3-yl)acetic acid, compound (I.5)

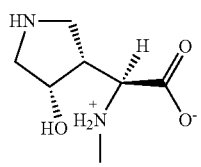

3,4-cis 3-(1,2-diaminoethyl)-4-hydroxy-pyrrolidine, compound (I.6)

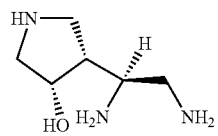

as well as their pharmaceutically acceptable salts, solvates or hydrates.

12. Pharmaceutical compositions containing a derivative of pyrrolidine according to claim 1, with at least one pharmaceutically acceptable excipient.

\* \* \* \* \*